United States Patent [19]

Gelfand et al.

[11] Patent Number: 4,784,949

[45] Date of Patent: Nov. 15, 1988

[54] UNIVERSAL DOMINANT SELECTABLE MARKER CASSETTE

[75] Inventors: David H. Gelfand; Frances C. Lawyer, both of Oakland; Susanne Stoffel, El Cerrito, all of Calif.

[73] Assignee: Cetus Corporation, Emeryville, Calif.

[21] Appl. No.: 602,118

[22] Filed: Apr. 19, 1984

[51] Int. Cl.[4] .................... C12P 21/00; C12N 15/00; C12N 1/20; C07H 15/12

[52] U.S. Cl. .................... 435/68; 435/172.3; 435/253; 435/254; 435/255; 435/320; 536/27; 935/14; 935/27; 935/28; 935/29; 935/47

[58] Field of Search .................... 435/68, 172.3, 317; 935/10, 14, 22, 27, 47

[56] References Cited

FOREIGN PATENT DOCUMENTS 2091268 7/1982 United Kingdom.
2100738 1/1983 United Kingdom.

OTHER PUBLICATIONS

Southern et al 1982 "Transformation of Mammalian Cells to Antibiotic Resistance with a Bacterial Gene...", *J Mol Appl Gen* v1 327–341.
Oka et al 1981 "Nucleotide Sequence of the Kanamycin Resistance Transposon Tn 903", *J Mol Biol* v147 217–226.
Colbère-Garapin et al 1981 "A New Dominant Selective Marker for Higher Eukaryotic Cells", *J Mol Biol* v150 pp. 1–14.
Thompson et al 1983 "Nucleotide Sequence of a Streptomycete Aminoglycoside Phosphotransferase Gene...", *Proc Natl Acad Sci* v80 5190–5194.
Jimenez et al 1980 "Expression of a Transposable Antibiotic Resistance Element in *Saccharomyces*", *Nature* v287 p. 869.
Fraley et al 1983 "Expression of Bacterial Genes in Plant Cells", *Proc. Natl Acad Sci* v80 4803–4807.
Webster et al 1983 "Direct Selection of *Saccharomyces cerevisiae* Resistant to the Antibiotic G418...", *Gene* v26 pp. 243–252.
Sharp, P. A., et al *J. Mol. Biol.* (1973) 75:235-255.
Jorgensen, R. A., et al Molec. Gen. Genet. 177, 65–72 (1979).

*Primary Examiner*—Thomas G. Wiseman
*Assistant Examiner*—Thomas D. Mays
*Attorney, Agent, or Firm*—Albert P. Halluin; Kate H. Murashige

[57] ABSTRACT

A novel universal dominant selectable marker cassette is disclosed. The marker comprises the coding sequences for aminoglycoside phosphotransferase I (APH-I) which has been modified and truncated so as to render its use in recombinant vectors more convenient. The modified, truncated sequence (mtAPH-I) gene is capable, upon expression, of conferring resistance to a number of antibiotics on the host. One of these antibiotics, G418, is toxic to eucaryotic as well as procaryotic hosts. Also disclosed are methods of constructing fusion proteins having N-terminal sequences corresponding to a desired peptide sequence, and C-terminal sequences comprising the amino acids encoded by mtAPH-I.

29 Claims, 8 Drawing Sheets

| Plasmid | DNA Sequence & Deduced Amino Acid Sequence | MIC – 50% |
|---|---|---|
| pNG56 | AAGGGGTGTT ATG...TGC TCG AGG CCG CGA TTA AAT TCC AAC ATG GAT<br>             Met...Cys Ser Arg Pro Arg Leu Asn Ser Asn Met Asp<br>              1     10  11  12  13  14  15  16  17  18  19  20 | >300 μg/ml |
| MCK 4.1 | AAGCTT ATG TCG AGG CCG...<br>       Met Ser Arg Pro...<br>        1   2   3   4 | >300 μg/ml |
| MCK 1.4 | AAGCTT ATG TGT TCG AGG CCG...<br>       Met Cys Ser Arg Pro...<br>        1   2   3   4   5 | >300 μg/ml |

FIG.5

UNIVERSAL DOMINANT SELECTABLE MARKER CASSETTE

TECHNICAL FIELD

The present invention relates to aspects of recombinant DNA technology concerned with providing markers for genetic transformation. More particularly, the invention relates to a convenient dominant selectable marker system suitable for use in both procaryotes and eucaryotes, and for use in synthesis of dominant selectable fusion proteins.

BACKGROUND ART

Alteration of the genetic makeup of a host cell is the modus operandus of current biotechnology. By suitable modification, such host cells may be caused to produce protein sequences normally unavailable in large quantity, for example, the fibroblast or leukocyte interferons; or their metabolism may be altered so as to induce them to perform some unaccustomed function such as, for example, the conversion of starch to simple sugar. A number of techniques for altering the genetic makeup of a host organism are known, including transduction and mutation. By far, however, the most useful technique in specific control of such genetic alteration is transformation of a host cell with a suitable recombinant vector, typically a plasmid. Depending on the host cell used, a variety of transformation conditions is used. Such conditions do result in transformed cells; however, the frequency of transformation may be relatively low, i.e., about 1 cell per $10^3$ for procaryotic hosts, and from one cell per $10^7$ to one cell per $10^2$ for eucaryotic hosts. Therefore, it is essential that a selection procedure be available to screen the population of host cells for the relatively few transformants. Typically this is achieved by including a sequence encoding a marker(s) on the transforming vector. Such a marker confers a phenotypic characteristic which will permit successful transformants to grow under conditions which are not capable of supporting the growth of the non-transformed cells.

Markers useful in procaryotic systems are well known and their use has become substantially routine. Such markers include Amp ®, a DNA sequence which encodes β-lactamase, an enzyme capable of degrading ampicillin, thus permitting the organism to grow in media containing the antibiotic; Tet ®, an analogous sequence for protection against tetracycline; and gene sequences encoding proteins which confer resistance to chloramphenicol, neomycin, and a number of other antibiotics. Plant cell transformations have often relied on infection with vectors such as those associated with *Agrobacterium tumefaciens* which confer selectable (but undesirable) traits on the transformants. These traits include overproduction and premature production of plant hormones, so that tumors result.

Selectable markers which are useful in other eucaryotic cells are not quite so well established. Some well known markers include the LEU2 gene which encodes the protein, β-isopropyl malate dehydrogenase, and thus permits a host organism which is normally incapable of synthesizing leucine (most commonly a (LEU2−) yeast mutant) to grow in the absence of leucine; a herpes virus thymidine kinase marker (TK) which is a sequence encoding this enzyme essential for DNA synthesis and thus permits the growth of mutant (tk−) organisms otherwise deficient in it; a sequence which encodes dihydrofolate reductase (DHFR) which permits growth in DHFR deficient strains; and xanthine-guanosine ribosyl transferase (XGRT), which similarly replaces a deficiency in this enzyme. Such markers were employed in the processes for transforming eucaryotic cells disclosed by Axel, et al, in U.S. Pat. No. 4,399,216.

It will immediately be noted that eucaryotic markers typically exert their effect by replacing a deficiency in the host, in the case of mammalian or yeast cells, or by conferring undesirable characteristics in the case of plants. Thus, these markers are not suitable for selecting transformants of a population of wild-type eucaryotic cells. This is clearly disadvantageous, as it confines recombinant manipulations to laboratory strains of eucaryotes and cultures of mammalian cells which are in some way abnormal. It precludes their use in industrial eucaryotes, such as ordinary Baker's yeast, and forces recombinant production of protein conducted in mammalian or plant cells to employ hosts which have (often undesirable) abnormalities, such as a malignancy or to confer undesirable characteristics on the transformed host.

This deficiency has particular impact with respect to attempts to utilize recombinant techniques in industrial strains of yeast. There is a reservoir of commercial experience in handling these strains, and they have been developed to have desirable fermentation properties, e.g., high level ethanol production, formation of desirable secondary metabolic products; to have desirable physical properties, e.g., flocculation; and to grow on inexpensive minimal nutrients. The lack of a dominant (to wild type) selectable marker operable in cells confines the yeast recombinant technology to the more sensitive and fastidious laboratory strains and effectively constitutes a bar to commercial utilization of recombinant yeast.

In summary, the recombinant techniques which have been, in the past decade, used successfully to transform procaryotic hosts with expression systems for desired protein products or desired metabolic characteristics, and which have relied on selection of transformants using co-transforming markers, could be extended to eucaryotic systems, including plants, mammals, and industrial yeasts, if an effective marker permitting selection of successfully transformed wild type hosts were available. Such marker would permit selection of eucaryotic transformed hosts capable of, for example, producing any desired proteins. Desired proteins would include, among others, the interferons, hormones, enzymes, growth factors such as PDGF or CSF, toxin intermediates, or antigenic determinants for the manufacture of vaccines.

Recently, a selectable marker which is effective in confering a phenotype useful to distinguish transformed wild-type from untransformed wild-type cells has been studied. An aminoglycoside antibiotic, G418, is toxic not only to bacteria but to yeast, plant, and mammalian cells. Thus, a wide range of cells is unable to grow in its presence, absent a protective enzyme. The antibiotic is inactivated (via phosphorylation) by the enzyme activity referred to as aminoglycoside phosphotransferase (APH). Two different enzymes with this activity are known, APH-I and -II. The coding sequences for these enzymes are located on transposons Tn601 (also known as Tn903) (Sharp, P. A., et al, *J Mol Biol* (1973) 75:235, and on Tn5 (Jorgensen, R. A., et al, *Mol Gen Genet* (1979) 177:65), respectively. These two enzymes are unrelated except for their ability to inactivate G418, which they, in fact, effect with differing efficiencies; APH-I is approximately four times as effective as APH-II. In view of the toxicity of G418 to a wide variety of cells, the coding sequence for either of these enzymes becomes a candidate dominant selectable marker for use in a wide variety of hosts. The coding sequence for APH-I is, in fact, known and a 271 amino acid sequence for the enzyme has been deduced from it (Oka, A. et al, *J Mol Biol* (1981) 147:217).

Indeed, a number of workers have cloned systems which permit the expression of these sequences in non-bacterial hosts. Southern, P. J., et al *J Mol Appl Genetics* (1982) 1:327 showed that mammalian cells transformed with vectors containing the coding sequence for APH-II presumably under control of a SV40 viral promoter, acquired resistance to G418. Colbere-Garapin, F., et al, *J Mol Biol* (1981) 150:1 disclosed expression of the APH-II coding sequence in tk⁻ and in monkey and human cell lines. The vectors used for transformation contained the TK promoter, presumably in such position to effect the expression levels. However, the bacterial promoter was also retained when tk⁻ cells were used as hosts (though not when normal cells were used); transformation efficiency was extremely low in non-tk⁻ cells.

Jimenez, A., et al *Nature* (1980) 287:869 presumably achieved some expression of the APH-I gene in yeast by co-transforming the Leu⁻-host *Saccharomyces cerevisae* with a mixture of pYE13 containing a LEU2 marker and ColicinEI derivative plasmid carrying the desired APH-I gene sequence presumably under control of sequences either indigenous to ColEI or to the enzyme encoding segment. Expression was shown only following selection for Leu⁺. Thus, Jiminez did not disclose a method to utilize the APH-I gene as a selection tool. Whether or not selection could have been made using G418 resistance as a criterion is unclear. No effort was made by Jimenez to place the coding sequence under the control of a yeast promoter. It would thus be unlikely that the gene expression levels would be sufficient to provide amounts of protein effective against selection pressure (as opposed to the ability of selected cultures to exhibit G418 resistance).

Fraley, R. T., et al *Proc Natl Acad Sci (U.S.A.)* (1983) 80:4803 describe the utilization of the coding sequence from the APH-I gene under control of a promoter derived from a bacterium capable of infecting plants, and terminated with a 3' untranslated terminating sequence also active in plants. Presumably under such control, expression of the gene for this enzyme, and also for the related APH-II analog was achieved in petunia cells. Finally, U.K. patent application No. GB2100738A, published Jan. 6, 1983, discloses expression of both the gene encoding APH-I and that encoding a protein which confers resistance to hygromycin B under the control of an SV40 promoter. Expression was achieved both in yeast and in mammalian mouse Ltk- cells.

Webster, T. D., et al, *Gene* (1983) 26:243 disclose the use of native APH-I as a selection marker useable after 18 hours from transformation in laboratory yeast strains.

In all of the above cases, the coding sequence for the desired G418 resistance gene was preceded by an uncontrolled number of nucleotides between the ntural ATG start codon and the control sequences and, indeed, the nearest upstream convenient restriction site which might permit manipulation with respect to such control sequences. As a result, random occurrences of ATG codons and TGA, TAA, or TAG termination codons in various reading frames in this preceding sequence interfere with a precise reproducible translation of the desired sequence. In addition, because the start codon is not immediately downstream from a convenient restriction site, it has not been possible to synthesize fusion proteins which contain the APH-I sequences at the C-terminal end. Thus, it has not been possible to use such a construction as a fusion flag whereby, analogous to the situation with β-galactosidase, a selectable characteristic is conferred on a desired fusion protein. Such selectable fusion proteins are useful in optimizing the expression of the coding sequence for desired proteins fused to the N-terminal end of the flag, as well as in stabilizing peptide products which may be heterogeneous and unfamiliar to the host organism. If the techniques and vectors for so utilizing it were available, the employment of a marker such as APH-I in a fusion sequence would permit it to be used as an extremely convenient "affinity signal" for the purification of the complete fusion protein from the rest of the cellular milieu. In addition, such a fusion sequence may be used to confer added immunogenicity on the desired short peptide immediately preceding it.

Thus, what is desirable over and above the constructions now known in the art is a dominant selectable marker cassette which has restriction sites immediately preceding its start codon so as to permit, first, efficient construction of expression vectors and, second, production of fusion products. These capabilities will permit efficient selection of transformants in wild type eucaryotic systems, enable precise control of the expression of genes for desired sequences (as N-terminal sequences of the fusion proteins) in both procaryotic and eucaryotic hosts and (also as fusion proteins) will provide desired proteins with stabilization, immunogenicity, and desirable characteristics for purification.

DISCLOSURE OF THE INVENTION

The present invention provides a truncated coding sequence for APH-I (hereinafter sometimes called the Kan gene) which contains convenient restriction sites immediately upstream of the start codon. The coding sequences of this marker can be used as a cassette and integrated into plasmids containing control sequences such as promoters and transcription termination sequences which are effective in any desired host organism. Thus, the coding sequence can be shuttled from a carrier vector into a vector adapted to replication and expression in yeast or one which is adapted to expression and replication in a number of other types of organisms such as procaryotes, plants, and mammalian cells.

In providing this cassette, the invention also permits construction of fusion proteins which contain the sequences conferring G418 resistance conjugated to the C-terminus of a desired peptide sequence. This desired sequence may contain a particular antigenic component or may be unstable in the cellular medium by virtue of its size, and its synthesis as a fusion protein will thus provide necessary immunogenicity or stability, respectively. Such fusion proteins have additional utilities: (1) they provide assay systems which are capable of assessing the effectiveness of expression control sequences which are operably linked to the desired peptide, and (2) they can be used as an affinity recognition sequence for purification.

Thus, in one aspect, the invention relates to a DNA sequence encoding a modified truncated Kan gene and having at least one cassette-unique restriction site upstream of, and proximal to, the ATG start codon of the modified, truncated Kan gene. In two preferred embodiments, the truncated Kan gene is missing the codons 2-9, and 2-10, respectively, and has been modified to destroy the HindIII and XmaI sites at codon positions 184/185 and 102/103 of the non-truncated gene sequence. Thus, this aspect of the invention provides a modified, truncated Kan gene (mtKan or mtAPH-I) cassette which is adaptable to a variety of uses.

In other aspects, the invention relates to cloning and expression vectors which contain the modified, truncated Kan gene cassette of the invention operably linked to control sequences suitable for a particular host. Such vectors may also include expression sequences for a desired peptide; the presence of an effectively expressible mtAPH-I thus serves to provide a selection tool for cells capable of providing the desired protein. In other vectors of the invention, a DNA sequence encoding a desired protein is placed in reading frame with the modified, truncated Kan gene coding sequence, and operably linked to suitable control sequences, so that expression of these sequences results in a fusion protein.

Other aspects relate to host cells transformed with the above mentioned vectors, to the fusion protein products of transformants derived from these vectors, and to methods of obtaining such vectors, transformants, and fusion proteins. In yet still another aspect, the invention relates to the uses of the mtKan gene cassette as a dominant selectable marker in both procaryotic and eucaryotic cells, and to use of the fusion proteins produced as tools for stabilization or purification of a desired contained peptide sequence, or for conferring immunogenicity on the desired sequence.

BRIEF DESCRIPTION OF THE DRAWINGS

FIG. 5 shows the 5′ terminal coding sequences for the Kan gene in pNG56, pMCK4.1 and pMCK1.4, along with the corresponding N-terminal amino acid sequences, and the levels of Kan resistance conferred on E.coli MM294 by transformation with these vectors.

MODES FOR CARRYING OUT THE INVENTION

A. Definitions

Figure 1:
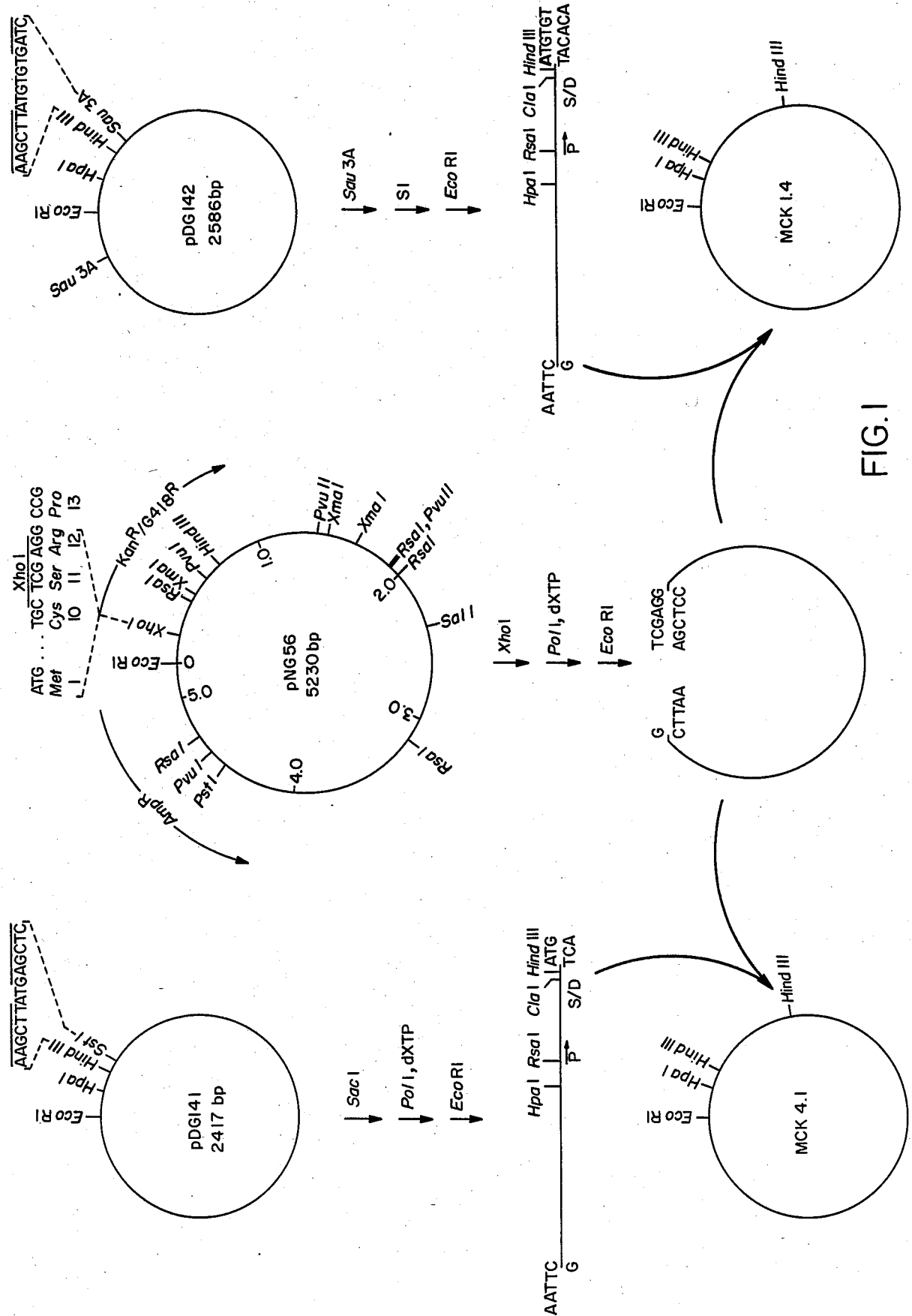
FIG. 1 shows the construction of pMCK4.1 and pMCK1.4.

As used herein, "Kan gene" (or APH-I gene) refers to a DNA sequence encoding a protein which is capable of exhibiting the functional characteristics of APH-I. These functional characteristics include inactivating a series of antibiotics, and APH-I is distinguishable from APH-II and from the enzyme inactivating hygromycin B by virtue of the spectrum of activities it exhibits. Thus, although termed the "Kan gene" herein for brevity and convenience, the protein encoded by this gene is considerably less effective in inactivating kanamycin than is the related protein APH-II. It is, however, somewhat more effective in inactivating neomycin and considerably more so in inactivating lividomycin against which its analogous counterpart is completely inactive. However, the protein encoded by this gene is approximately four times as effective against G418 as the APH-II enzyme. This is particularly advantageous because of the toxicity of G418 against a wide range of cells including eucaryotes.

"Truncated Kan gene" or tAPH-I refers to a Kan gene coding sequence which has been abbreviated in some fashion. Generally, this terminology is used with respect to the truncated forms disclosed by this invention: i.e., the "∇2-9" and "∇2-10" deletions. However, other deletions which retain the functionality of the resulting protein are also within the scope of the invention.

"Modified Kan gene" or mAPH-I gene refers to a Kan gene or, if appropriate from the context, truncated Kan gene wherein the base sequence is altered so as to allow the amino acid sequence encoded to remain the same while altering the restriction site pattern within the gene. Specifically, it refers to such modifications which eliminate restriction sites within the gene which sites would otherwise destroy the unique nature of a cassette-unique site (defined below).

"Modified, truncated Kan gene" or mtAPH-I refers to a Kan gene which is both modified and truncated as described in the preceding two paragraphs.

"Cassette-unique" restriction site refers to a site for specific endonuclease digestion which appears only once in the DNA sequence desired to be excised. Thus, most relevant to the present invention, the Kan gene encoding sequence is modified to remove any recognition sites which are identical to those available to excise or manipulate the cassette.

"Proximal to" when used to describe the location of a cassette-unique restriction site in relation to a ATG start codon for a desired coding sequence means that the site is positioned with respect to the ATG start codon in such a way that there are no intervening ATG or stop codon sequences between the site and the desired ATG start codon. In addition, the site must be sufficiently close to the desired ATG start that it permits operable linkage (as defined below) to a promoter sequence and, if applicable, a ribosome binding site sequence upstream of the site. Thus, two criteria must be met: lack of alternate false start or stop signals, and reasonable spacing to permit the desired coding sequence to be expressed when religated into appropriate expression vectors.

"Operably linked" refers to constructions wherein the components so described are juxtaposed in such a way as to permit them to function in their intended manner vis-a-vis each other. Thus, a promoter operably linked to a coding sequence refers to a promoter which is capable of effecting the transcription of the desired coding sequence.

"Suitable for" or "appropriate to" eucaryotic or other cells refers to control sequences which, when found in nature, would ordinarily control the expression of coding sequences in a particular type of cell or are more than marginally effective in doing so. For example, promoters suitable for eucaryotic cells include the SV40 early promoter which is, in fact, a viral promoter. However, the mode of operation for the virus is to cause transcription to occur by virtue of this promoter using the machinery of a mammalian cell. Similarly, the nopaline synthase promoter of *Agrobacterium tumefaciens* operates effectively in the eucaryotic plant cell it infects. Various yeast promoters, such as LEU2 or ENO1, are found to effect expression of proteins in yeast, and hence are "appropriate to yeasts". To the extent any particular control sequence(s) effect successful expression of an operably linked sequence in a host, such sequence(s) would be considered to fall within this definition.

"Control sequences" refers to whatever is required to effect the expression of a coding sequence in connection with a particular host. It is clear that in both procaryotic and eucaryotic systems appropriate promoters, with or without operators, are required. Procaryotic hosts also require presence of a ribosome binding site. It appears that eucaryotic cells generally require, for effective expression, a polyadenylation signal to assure that the mRNA transcribed from the gene sequences is transported out of the nucleus and translated. The nature of this process is not well understood, but it is known that certain terminator sequences which include polyadenylation signals are necessary for effective production of desired proteins in eucaryotic hosts. Suitable "signal" sequences include the ENO1 3' untranslated region from the ENO1 gene, and the nopaline synthase sequences obtainable from Agrobacterium plasmids which normally operate in the plant cell host.

"Polyadenylation signal" or "terminator" is intended to include whatever is required in these sequences, not to be limited simply to this particular function. This definition is necessitated by the current state of knowledge in the art, wherein the relevance of sequences in addition to the polyadenylation signal is unclear.

B. General Description

The modified, truncated Kan gene cassette of the invention can be used in a variety of contexts and constructions. Its advantages, as stated above, are its universality as a marker system in a wide variety of transformed hosts, its transportability from one expression vector to another, and its provision of proximal 5' restriction cassette-unique endonuclease recognition sites so as to permit its inclusion as a C-terminal sequence fusion protein or its operable linkage to suitable control sequences. Thus, it may be used as follows:

1. It may be ligated in operable linkage to promoters (and/or terminators) suitable to a variety of host cells, as part of expression vectors, and then used as a dominant selectable marker for direct selection of successful transformants in the same sense ampicillin resistance can be so used in the commonly employed procaryotic transformations. Such expression vectors include, for example, pFC19 and pDG151, wherein the gene is under the control of the trp promoter system. These also contain restriction sites for insertion of other expression sequences, thus coding and control sequences for a desired protein may also be inserted into them, and the phenotypic property conferred by the mtAPH-I gene used as a selectable marker for successful transformants. These vectors are suitable for procaryotic expression, as is pPLKan illustrated herein. Analogously, for eucaryotes, pDG148 contains the modified, truncated Kan cassette under control of SV40 promoter, and convenient sites for insertion of additional expression sequences; similarly pDG151::RSV contains the Rous Sarcoma Virus "LTR" promoter. Plasmid pDG149 contains the modified, truncated Kan cassette under control of the enolase promoter and terminator from yeast; pDG150 is a slightly smaller form of pDG149 wherein the bacterial-derived sequences preceding the yeast enolase promoter sequences are deleted. These plasmids and others like them are, of course, merely illustrative, and they can be used as backbone expression vectors which contain a simple index of successful transformation in a variety of hosts which can be, then, employed in transformation to obtain production of desired protein sequences encoded under suitable control in inserts made to these vectors. In order to function in this way, the vectors need only have an origin of replication or other means of replication (such as integration into the genome) compatible with the host, the mtAPH-I sequence operably linked to control sequences suitable to the host, and at least one unique restriction site not present in the mtAPH-I expression sequences.

2. The truncated Kan sequence can be used as a fusion flag when a suitable expression sequence is ligated upstream of its 5' terminus. Because it can be (and, indeed, has been) provided with convenient restriction sites immediately prior to its ATG start codon, construction of such fusion proteins is feasible. Thus, for example, the plasmids, pDG144 and pDG151, permit insertion of the initiation control and coding sequence for portions of, for example, a LEU2 gene (which can be expressed both in *E. coli* and in yeast) and results in a fusion between the sequence encoding the enzyme, β-isopropyl malate dehydrogenase (permitting leucine independence in LEU2− (yeast) and leuB− (*E.coli*) hosts), and the modified truncated Kan sequence. The effect of changes in the control system for the LEU2 gene can then be studied by using the expression of the Kan sequence as an indicator, since the level of G418 resistance can be used as an index for level of expression of the gene encoding the fused peptide sequence. Again, these embodiments are illustrative only; the requirements for the host vector are ability to replicate and express mtAPH-I in a cloning (not necessarily the desired) host and a cassette-unique restriction site upstream of, and proximal to, the mtAPH-I ATG start codon. This permits the construction of expression vectors for fusion proteins wherein the N-terminal sequence and 5' control sequences suitable to the intended host are linked to the mtAPH-I coding sequence at the C-terminus. For eucaryotic hosts, it may also be required and probably desirable to include 3' control sequences downstream from the mtAPH-I codons, however, this is not at present clear. Additional utilities of the resulting fusion proteins are suggested in paragraphs 3–5 below.

3. By using, as the N-terminal fusion partner, the codons for an antigenic sequence, an immunogenic fusion protein will result, thus permitting the modified, truncated Kan sequence to serve to confer both a selectable characteristic on the transformant and added immunogenicity on the antigen. This is especially significant since antigenic determinants are often quite short amino acid sequences which are not immunogenic. Such immunogenic proteins are particularly useful for diagnostic and therapeutic (vaccination) purposes.

Thus, in addition to, for example, pLK11.17, pLK51.57, and other fusion protein encoding vectors illustrated herein, alternate vectors containing control and coding sequences for other N-terminal fusion partners such as, for example, the antigenic determinant peptide portions of viral coat proteins, may be constructed using means known in the art.

4. The fusion proteins made possible by the modified, truncated Kan cassette of this invention can also be produced as stabilized forms of short polypeptide segments as N-termini in a variety of hosts.

5. The fusion proteins can be purified by aminoglycoside affinity chromatography by taking advantage of the specific aminoglycoside binding ability of the mtAPH-I portion of the peptide. Conditions for affinity chromatography based on such enzyme substrate binding are much milder than those associated with antigen-/antibody affinity separations, thus minimizing the danger of destroying the desired protein when eluting it from the support.

The specific embodiments described below illustrate the construction of vectors which are useful in the foregoing utilities. pFC19 is particularly useful for diagnosis of regulatory systems in procaryotic hosts. It contains the modified, truncated Kan sequence immediately downstream from a HindIII site, a cassette-unique restriction site which is the 3' end of an EcoRI/HindIII trp promoter/operator cassette and proximal to the ATG start codon. (The native Kan coding sequence is modified to destroy the HindIII site at codons 184/185.) Thus, expression of the modified, truncated Kan gene sequences can be used to indicate the power of substitute control systems for the trp cassette.

pDG144 provides a versatile source for the modified, truncated Kan cassette of the invention. In the DNA sequence immediately 5' of the ATG start codon of $\nabla$2-10 truncated Kan coding sequence, there are convenient HindIII, BamHI, SmaI, and EcoRI cleavage sites; the HindIII (codons 184/185) and SmaI (codons 102/103) sites in the native coding sequences have been destroyed. Thus, promoters and desired coding sequences for fusion proteins having a variety of 3' restriction sites can be placed in reading frame preceding the ATG start codon.

pDG148 and pDG151::RSV illustrate the insertion of the modified truncated Kan cassette into vectors containing (in pDG148) a mammalian origin of replication (from SV40) and SW40 or RSV derived transcription control sequences. By placing a desired coding sequence under the control of an additional eucaryotic promoter, and inserting the package elsewhere in the pDG148 or pDG151::RSV plasmids, pDG148 or pDG151::RSV can be used as suitable backbone fragments containing a dominant selectable marker. Also, by insertion of a desired protein coding sequence into the convenient cassette-unique HindIII site between the promoter and the ATG codon of the truncated modified Kan gene with or without its own promoter sequence, a desired protein sequence can be produced in eucaryotic cells as a fusion protein, and successful expression of the sequence detected by use of the Kan gene as a fusion flag. In either case, by increasing the concentration of G418 in the medium in which the cells are grown, those which are particularly successful in producing the Kan gene product, and, therefore, in producing the desired protein sequence can be selected.

pDG149 and pDG150 illustrate analogous constructions which are particularly appropriate in transformation of yeast. The plasmids contain the modified truncated Kan sequence under control of the enolase I promoter and termination sequences. Insertion of a desired coding sequence under control of an additional yeast promoter at one of the other restriction sites in these plasmids can be used to produce a desired protein with the aid of selection for successful high copy number transformants utilizing increasing G418 concentration in the medium.

The foregoing plasmids are, of course, merely illustrative of vectors suitable for eucaryotic hosts which will accept additional expression cassettes or coding sequences and provide the ability to replicate in eucaryotes and effect the production of a dominant selectable marker. Analogous plasmids can be constructed, for instance, by using mtAPH-I cassettes encoding the $\nabla$2-9 protein constructed from MCK1.4 (¶D.1.b.1) in a manner precisely similar to that which was employed in constructing the mtAPH-I cassette encoding a $\nabla$2-10 protein from MCK4.1 (¶D.1.a.3)

pDG151 is a modification of pDG149 which is even more convenient for construction of fusion proteins having the mtAPH-I sequence at their C termini. By providing a multiplicity of cassette-unique restriction sites 5' of the mtAPH-I gene, partial or complete coding sequences under control of suitable promoters can be fused to the mtAPH-I coding sequences which, in pDG151,, have been provided with a terminator operable in yeast, resulting in a fusion protein with a kanamycin/g418 resistance fusion flag.

C. Methods Employed

Both cloning and expression vectors for desired sequences were constructed using the below described commonly employed restriction and ligation procedures. Additional plasmids, analogous to those illustrated, can also be constructed using these methods, which are well known in the art, by utilizing alternative replicons, vector fragments, control sequences, coding sequences, polylinkers, and expression cassettes.

In general, the quantity of DNA available can be increased by cloning the desired fragments, i.e., inserting into a suitable cloning vehicle, such as pBR322, transforming and replicating in *E. coli*, and, optionally, further enhancing through chloramphenicol amplification or by phage replication. For expression, the desired fragments can then be removed from the cloning vectors or phage and ligated to suitable control sequences compatible with the host intended to be employed in the expression of the gene. Such hosts are then transformed with these expression vectors and cultured under conditions which favor stabilization of the plasmid and the safe production of a desired protein fragment. Such conditions might include repression of the controlling promoter until most of log phase has been completed, and then alteration of conditions so as to favor the synthesis of the peptide.

C.1 Control Sequences and Hosts

As the marker cassette of the invention is intended to be utilized in a variety of hosts, it is incorporated into expression vectors containing promoters and any other requred control sequences suitable for the appropriate host cell. Vectors compatible with procaryotes, and suitable for transformation of such vectors into these host cells are described with respect to use of *E. coli* K12 strain, MM294 or, in some instances, a lambda lysogen of *E. coli* strain MC1000 and are set forth in detail. However, other microbial strains may also be used, such as bacilli, for example *Bacillus subtilis,* various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli pk* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences which are defined herein to include transcription initiation, optionally with an operator, along with ribosome binding site sequences, include such commonly used promoters as the betalactamase (penicillinase) and lactose (lac) promoter systems (Chang et al, *Nature* (1977) 198:1056 and the tryptophan (trp) promoter system (Goeddel, et al, *Nucleic Acids Res* (1980) 8:4057 and the lambda derived $P_L$ promoter and N-gene ribosome binding site (Shimatake, et al, *Nature* (1981) 292:128), which has been made useful as a portable control cassette, as set forth in copending Application Ser. No. 578,133, filed Feb. 8, 1984, and assigned to the same assignee. However, any available promoter system compatible with procaryotes can be used.

In addition to bacteria, eucaryotic microbes, such as yeast, may also be used as hosts. Laboratory strains of *Saccharomyces cerevisiae,* Baker's yeast, are most used although a number of other strains are commonly available. While vectors employing the 2 micron origin of replication are illustrated, Broach, J. R., *Meth Enz* (1983) 101:307, other plasmid vectors suitable for yeast expression are known (see, for example, Stinchcomb, et al, *Nature* (1979) 282:39, Tschempe, et al, *Gene* (1980) 10:157 and Clarke, L., et al, *Meth Enz* (1983) 101:300). Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. In the constructions below, the 3' untranslated region of the enolase' gene is used; alternate sources for such sequences are available in the art. Many of the vectors illustrated contain control sequences derived from the enolase gene containing plasmid peno46 (Holland, M. J., et al, *J Biol Chem* (1981) 256:1385) or the LEU2 gene obtained from pYE13 (Broach, J., et al, *Gene* (1979) 8:121), however any vector containing a yeast compatible promoter, origin of replication and other control sequences is suitable.

It is also, of course, possible to express genes encoding polypeptides in eucaryotic host cell cultures derived from multicellular organisms. See, for example, *Tissue Cultures,* Academic Press, Cruz and Patterson, editors (1973). Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papiloma virus, or avian sarcoma viruses. Origins of replication may be obtained, if needed, from similar sources. However, integration into the chromosome is a common mechanism for DNA replication in eucaryotes. Plant cells are also now available as hosts, and control sequences compatible with plant cells such as the nopaline synthetase promoter and polyadenylation signal sequences (Depicker, A., et al, *J Mol Appl Gen* (1982) 1:561) are available.

C.2 Transformations

Depending on the host cell used, transformation is done using standard techniques appropriate to such cells. The calcium treatment employing calcium chloride, as described by Cohen, S. N., *Proc Natl Acad Sci (U.S.A.)* (1972) 69:2110 is used for procaryotes or other cells which contain substantial cell wall barriers. Infection with *Agrobacterium tumefaciens* (Shaw, C. H., et al *Gene* (1983) 23:315) is used for certain plant cells. For mammalian cells without such cell walls, the calcium phosphate precipitation method of Graham and van der Eb, *Virology* (1978) 52:546 is preferred. Transformations into yeast were carried out according to the method of Van Solingen, P., et al, *J Bact* (1977) 130:946 and Hsiao, C. L., et al, *Proc Natl Acad Sci (U.S.A.)* (1979) 76:3829. Briefly, yeast cultures grown to mid-log phase in YEPD rich medium (yeast extract, peptone and 4% glucose) were washed and protoplasted with zymolyase 5000 (Miles Laboratory) in sorbitol phosphate buffer. Protoplasts were washed, allowed to stand at room temperature for one hour in 67% YEPD containing 1M sorbitol, then pelleted and suspended in Tris-sorbitol-calcium chloride buffer to $2 \times 10^9$ protoplasts/ml. Protoplasts were mixed with 5–10 μg of DNA for transformation in a 100 μl reaction mix, then 1 ml of 44% PEG was added and the mixture allowed to stand for 40 minutes at room temperature.

C.3 Selection for G418 Resistance

For direct G418 resistance selection, dilutions of the transformation mixture were pipetted onto nutrient agar plates appropriate to the host (YEPD containing 1M sorbitol and 3% agar for yeast) and overlayed with 13 ml of the same nutrient agar (50° C.). After 2–6 hours incubating at 30° C., the plates were overlayed with 4 ml of similar medium (YEPD (2% agar) for yeast) and G418. The concentration of G418 for the total volume of agar on the plate (30 ml) was 100 to 250 μg/ml.

C.4 Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5-10 μm dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al (*J Am Chem Soc* (1981) 103:3185-3191). Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1-2 mM ATP, 1.7 pmoles $\gamma^{32}$ P ATP (2.9 mCi/mmole), 0.1 mM spermidine, 0.1 mM EDTA.

Ligations are performed in 15-30 μl volumes under the the following standard conditions and temperatures: 20 mM Tris-Cl pH 7.5, 10 mM MgCl$_2$, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations (usually employing a 10-30 fold molar excess of linkers) are performed at 1 μM total ends concentration.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per μg of vector at 60° for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

C.5 Verification of Construction

In the constructions set forth below, correct ligations for plasmid construction are confirmed by transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (U.S.A.)* (1969) 62:1159, following chloramphenicol amplification (Clewell, D. B., *J Bacteriol* (1972) 110:667). The isolated DNA is analyzed by restriction and/or sequenced by the dideoxy method of Sanger, F. et al, *Proc Natl Acad Sci (U.S.A.)* (1977) 74:5463 as further desribed by Messing, et al, *Nucleic Acids Res* (1981) 9:309, or by the method of Maxam, et al, *Methods in Enzymology* (1980) 65:499.

C.6 Hosts

Host strains used in cloning and expression herein are as follows:

For cloning and sequencing, and for expression of construction under control of most bacterial promoters, *E. coli* strain MM294 (supra), Talmadge, K., et al, *Gene* (1980) 12:235; Meselson, M., et al, *Nature* (1968) 217:1110, was used as the host.

However, when expression is under control of the procaryotic P$_L$ promoter and N$_{RBS}$ the *E. coli* strain MC1000 Lambda N$_7$N$_{53}$cI857SusP$_{80}$ as an expression host was used (ATCC 39531, deposited Dec. 21, 1983). This strain is hereinafter referred to as MC1000-39531.). This strain contains a lambda prophage which codes for a temperature sensitive CI repressor, which at the permissive temperature (30°-32° C.) is active. At the nonpermissive temperature (36°-44° C.), the repressor is inactive and transcription from the PL promoter can proceed. It is further characteristic of this strain that at elevated temperatures the prophage fails to induce.

Expression in yeast employed a laboratory strain of *S. cerevisiae* designated S173-6B, which is LEU2−, URA3−, TRP1−, HIS4−. This strain is obtainable from Professor Michael Holland, University of California, Davis. Industrial yeast *S.cerevisiae* strains used included Red Star distillers activated dry yeast (red Star Yeast Co., Oakland, Calif.); strain GB4722 obtainable from Dr. Anthony Rose, University of Bath, Bath, England; and CBS 6508, Centraal bureau Voor Schimmel cultures, Netherlands.

C.7 Verification of DNA Uptake

Transformations using yeast hosts were tested for uptake and replication of the desired sequences by DNA isolation and Southern Blot. DNA is isolated by the method of Sherman, F., et al, *Methods in Yeast Genetics* (1979), Cold Spring Harbor Laboratory. Briefly, after growth to late log phase in the appropriate selective medium (e.g., YEPD and 150 μg/ml G418), cells were washed and protoplasted with zymolyase 5000 (Miles Laboratory) in 1M sorbitol, 20 mM EDTA. The protoplasts were then pelleted and suspended in 0.15M NaCl, 0.1M EDTA, predigested pronase and SDS added and the protoplasts incubated one to three hours at 37° C. The mixture was heated to 70° C. for 15 minutes, put on ice, and potassium acetate added to 0.5M. After 30 minutes on ice, the mixture was centrifuged and the resulting supernatant treated with RNase and extracted with chloroform and isoamyl alcohol (24:1). The aqueous phase was centrifuged and the resulting supernatant ethanol precipitated, the precipitate was washed and resuspended, and the DNA precipitated with isopropanol.

Southern Blot analysis was done according to the method of Southern, *J Mol Biol* (1975) 98:503. Briefly, the isolated DNA was digested to completion with one or more restriction endonucleases, and run on agarose gels with molecular weight markers. DNA fragments were depurinated, in situ, with 0.075M HCl, denatured in 0.5M NaOH, 1.5M NaCl, and neutralized in 1M Tris-Cl pH 7.4, 3M NaCl. The DNA on the gels was transferred to nitrocellulose filters via diffusion blotting in 20×SSC overnight. The filters were then baked at 80° C. in a vacuum oven for two hours.

Before hybridization with probe, the nitrocellulose filters were prehybridized for 3 hours to overnight at 42° C. in 50% formamide, 5×SSC, 1/20 P/Pi (P/Pi is 0.05M sodium pyrophosphate, 0.5M sodium phosphate, monobasic, 0.5M sodium phosphate dibasic), 0.1% SDS, 5×Denhardt's (Denhardt's is 0.02% BSA, 0.02% Ficoll, 0.02% PVP), and 200 μg/ml sheared denatured carrier DNA.

The filters were hybridized with 106 cpm of (usually) $^{32}$P-labelled, nick-translated DNA probe in a solution of 50% formamide, 5×SSC, 1/20 P/Pi, 0.1% SDS, 2×Denhardt's, and 100 μg/ml sheared denatured carrier DNA at 42° C. for 18-24 hours.

The hybridized filters were washed three times in 2×SSC, 0.1% SDS at room temperature, dried and exposed to x-ray film.

D. Detailed Description of Preferred Embodiments

D.1 Construction of Vectors Containing Modified Truncated Kan Gene Under Trp Control D.1.a Construction of pFC19

Figure 2:
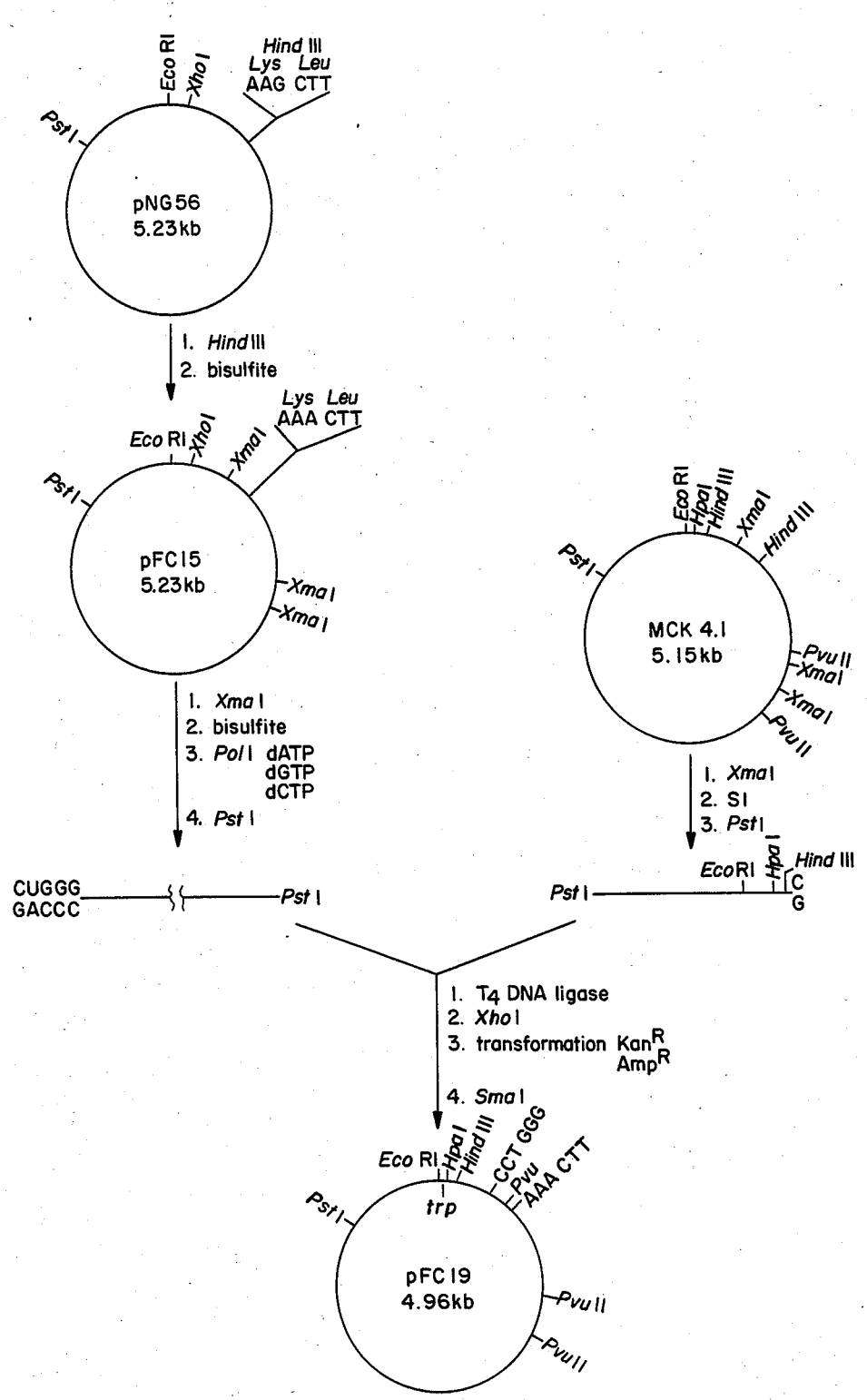
FIG. 2 shows the construction of pFC19.

The construction of pFC19 which contains mtAPH-I under trp control, is illustrated in FIG. 2. *E. coli* K12 strain MM294 harboring plasmid pFC19 was deposited with the ATCC on Dec. 22, 1983, and designated ATCC No. 39551.

As shown in FIG. 2, plasmid pFC19 is a ligation product of 5' PstI/blunt-3' DNA fragment containing the trp promoter and the N-terminal ∇2-10 APH-I coding sequence from plasmid MCK 4.1 and a mutated, 5'-blunt/PstI-3' DNA fragment from plasmid pFC15 containing a modified C-terminal APH-I sequence. The pFC15 derived fragment in pFC19 contains the majority of the coding sequence for Kan gene but with a site specific mutations which destroys the HindIII site that is present in the coding sequence, but retaining the meaning of the codons.

Both plasmid MCK4.1 and pFC15 were derived from pNG56, a plasmid containing the entire Kan gene coding sequence. The Kan coding sequence in pNG56 was shown to have a XhoI site at codons 10/11, it can thus be used to furnish the C-terminal codons 11-271 of APH-I by suitable digestion. pFC15 was derived from pNG56 by site specific mutagenesis, and contains a modification at codons 184/185 of the native sequence.

D.1.a.1 Construction of pNG56

Plasmid pNG56 is a derivative of pNG20 (Grindley, N. D. F., et al, *Proc Natl Acad Sci (U.S.A.)* (1980) 77:7176). pNG20 encodes only the carboxy-terminal portion and downstream inverted repeat of the 3 kb sequence of APH-I from Tn601 disclosed by Oka, A., et al, *J Mol Biol* (1981) 147:217 (i.e., nucleotides 1701-3094 of the Oka sequences) and thus fails to confer resistance to kanamycin.

pNG56 contains the entire Kan gene coding sequence but lacks, as does pNG20, the approximately 1.04 kb 5' (upstream) inverted repeat present in Tn 601. To obtain pNG56, pNG20 was treated with ClaI (which cuts uniquely upstream of the Tn 601 sequence) and with HindIII (which cuts at codons 184/185 of the coding sequence). The desired control and N-terminal coding sequences were added by isolating the appropriate fragments resulting from TaqI/XhoI and XhoI/HindIII digestion of pNG23, (Grindley, N. D. F., et al, (supra)) and performing a 3-way ligation of these two fragments with vector (ClaI and TaqI sticky ends are compatible). The ligation mixture was transformed into MM294 selecting for Amp®, Kan® and correct construction confirmed using standard methods.

D.1.a.2 Construction of pFC15 pNG56 was linearized with HindIII, and mutated with sodium bisulfite using the procedure of Shortle, D., et al, *Proc Natl Acad Sci (U.S.A.)* (1978) 75:2170. After removal of the bisulfite, the mutagenized DNA was ligated (redigested with HindIII), and used to transform *E. coli* K12 strain MM294. Kan® transformants were screened for plasmids which had lost a HindIII recognition site, and the successful plasmid constructions retransformed into *E. coli* MM294 for purification. Kan® transformants were again selected. The correct construction was verified by restriction enzyme analysis and sequencing. Codons 184/185 were verified to have been changed from

| AAG | CTT | to | AAA | CTT |
|-----|-----|-----|-----|-----|
| Lys | Leu |    | Lys | Leu. |

D.1.a.3 Construction of MCK 4.1

MCK 4.1 which was used to provide the trp promoter sequence and the truncated front end of the Kan gene was constructed from pNG56 and pDG141 as shown in FIG. 1 as follows:

pNG56 was digested to completion with XhoI, repaired with PolI Klenow fragment in the presence of all four dNTPs, and digested with EcoRI. The large approximately 5 kb fragment was isolated. It contains the coding sequence for all but the first ten codons of APH-I blunt ended so as to be in 0 reading frame with an upstream sequence.

pDG141 harbors the trp promoter operably linked to an ATG start codon, followed by a SacI site. It was deposited with the ATCC Jan. 24, 1984, and has accession number 39588. pDG141 was digested with SacI, treated with PolI as above, and digested with EcoRI. The small 116 bp promoter/ribosome binding site and ATG start codon fragment, which is blunt ended so as to be in 0 reading frame with a downstream sequence, was purifed by acrylamide gel electrophoresis and electroelution.

The pNG56 vector fragment and the promoter containing pDG141-derived fragment were ligated at about 200 μg/ml (1:1 molar ratio) under "sticky end" conditions, diluted fourfold, and the DNA fragments ligated under blunt-end conditions. The ligation mixture was used to transform E. coli MM294 and transformants selected for Amp® (50 μg/ml) and screened with increasing concentrations of kanamycin (5, 10, and 15 μg/ml). Plasmid DNA was isolated from Amp® Kan® (more than 10 μg/ml) and analyzed by restriction enzyme digestion and DNA sequence analysis. A successful construction, which was designated MCK4.1, yielded a unique HpaI DNA fragment, a 530 bp HindIII DNA fragment, and the expected altered RsaI digestion pattern.

D.1.a.4 Completion of pFC19 pFC15 was then itself mutagenized using the same technique following digestion with XmaI. The XmaI digested, mutagenized fragments from pFC15 were repaired with E. coli DNA polymerase I (PolI), Klenow fragment, in the presence of dCTP, dGTP, dATP, and then the flush ended DNA fragments digested with PstI and concentrated.

To prepare the MCK4.1 fragment, pMCK4.1 was digested with XmaI, treated with S1 nuclease under mild conditions (1 μl S1/150 μl reaction at 20° C., 20 min), and the fragments treated with PstI and concentrated.

The pFC15 and MCK 4.1 fragments were ligated at a 1:1 molar ratio using 0.62 μmole ends for 5 hrs at 4° C. using 40 μM ATP and then overnight at 14° C. using 1 mM ATP. The ligation mixture was digested with XhoI to inactivate the Kan promoter fragment of pFC15 and used to transform MM294. Colonies were selected in liquid medium containing ampicillin (50 μg/ml). The Amp® enriched transformed population was diluted and grown in medium containing Amp (50 μg/ml) and Kan (20 μg/ml) and plasmid DNA purified from a Amp® Kan® transformants. The plasmid preparation was digested with SmaI to eliminate nonmutants and retransformed into E. coli strain MM294. Plasmid DNA was isolated from Kan® Amp® colonies and the correct construction confirmed by restriction analysis and DNA sequencing. The desired construct was designated pFC19. In pFC19, the XmaI/SmaI site at codons 93/94 of the ∇2-10 tAPH-I sequence had been mutagenized so that codons 93/94 were altered from

```
CCC  GGG   to    CCT  GGG
Pro  Gly         Pro  Gly.
```

D.1.b. Construction of pFC19*

Using the procedures set forth in ¶ D.1.a., but substituting for MCK4.1, MCK 1.4, which was prepared as described in D.1.b.1, pFC19* is prepared. pFC19* is identical in every way to pFC19, except that the mtAPH-I has a 2-9 deletion rather than a 2-10 deletion.

D.1.b.1 Construction of MCK 1.4

MCK1.4 similar to MCK 4.1 except that it effectively contains a deletion of codons 2-9 rather than of codons 2-10. Codon 10 is supplied by pDG142, a plasmid similar to pDG141 except that it has a Sau3A site immediately downstream of the ATG and a succeeding, in frame, TGT cys codon. Thus, plasmid MCK 1.4 was obtained using a procedure similar to that set forth in D.1.a.3, but substituting for the 116 bp promoter/RBS/ATG fragment from pDG141, the isolated 119 bp promoter/RBS/ATG TGT fragment obtained by digesting pDG142 with Sau3A, treating with S1 nuclease, and digesting with EcoRI.

Plasmid MCK 1.4 was verified by restriction enzyme analysis and DNA sequencing to be precisely identical to plasmid MCK 4.1 except for the additional 3 bp TGT sequence following the start codon. Thus, MCK 1.4 may be used in precisely the same manner as was MCK 4.1 to obtain plasmids encoding a ∇2-9 APH-I protein.

D.2 Construction of mtAPH-I Vectors with 5' Polylinker Sequences

D.2.a. Construction of pDG144 and pFC20 pDG144 contains the coding sequence for the modified truncated Kan gene ∇2-10, immediately preceded by a linker fragment containing EcoRI, SmaI, BamHI, and HindIII restriction sites; in pFC20, this linker is also preceded by a duplicated lac operator, an inverted repeat of this linker, and the trp promoter. Both contain, distal to the 3' translation termination codon, convenient StuI, HaeII, BssHII, MstI and PvuII sites. pDG144 was constructed from pFC19 in several steps through pFC20 as an intermediate (see FIG. 4). pDG144 was deposited with the ATCC on Jan. 13, 1984, ATCC No. 39579.

Figure 3:
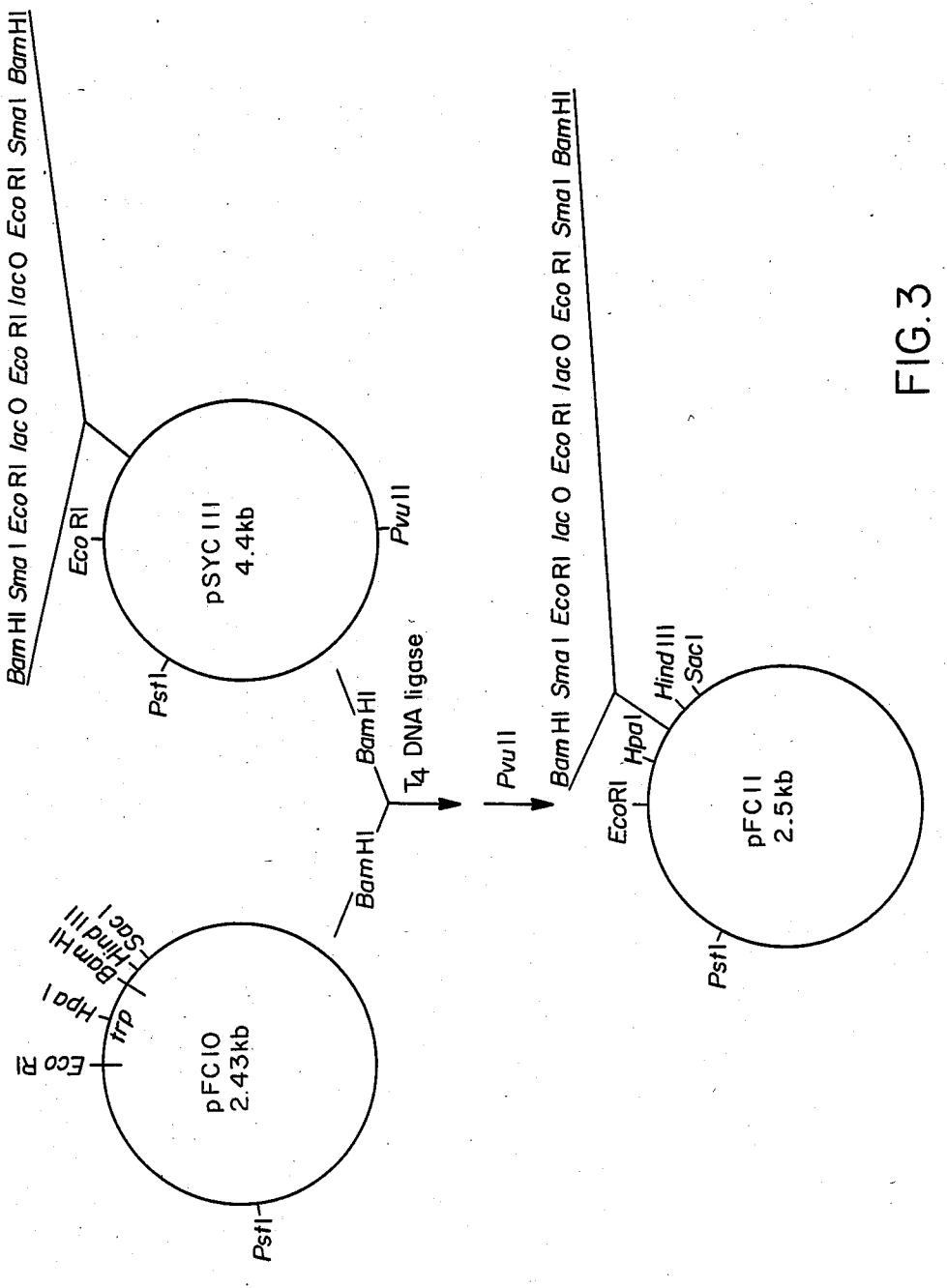
FIG. 3 shows the construction of pFC11.
Figure 4:
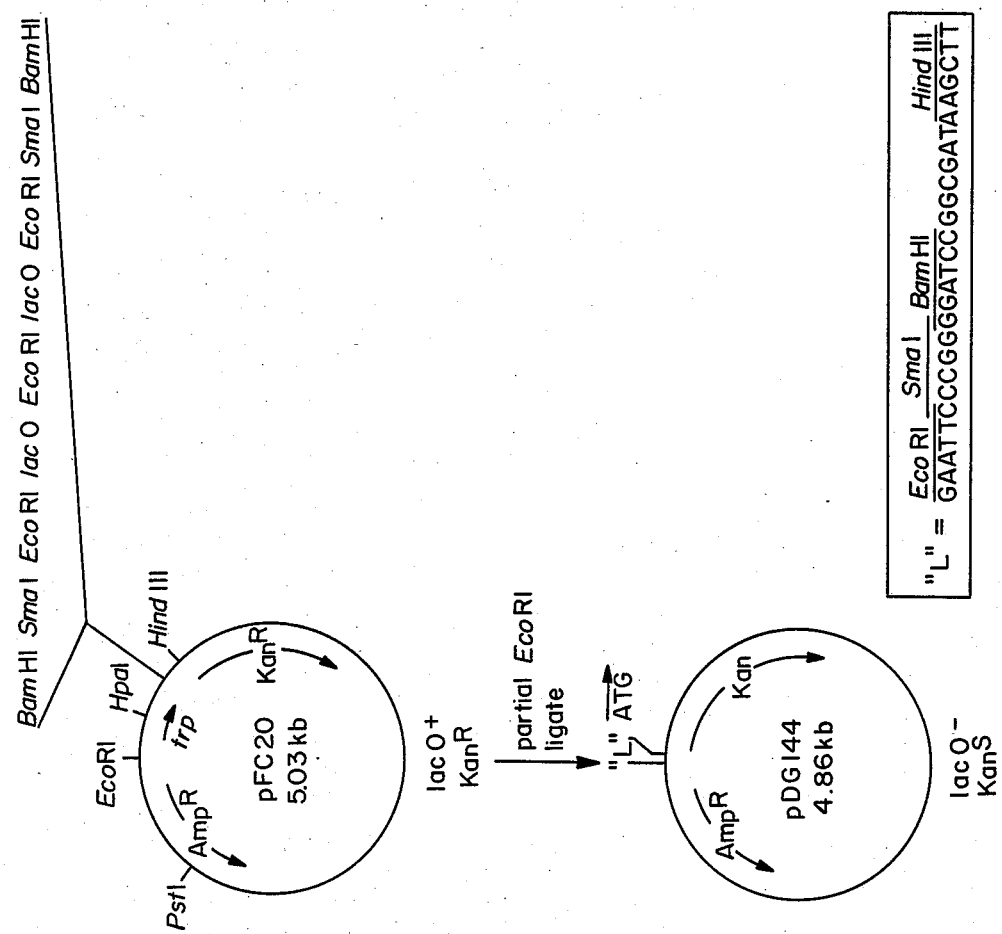
FIG. 4 shows the construction of pDG144.

D.2.a.1 Construction of pFC20 pFC19 was first digested with HpaI to inactivate the trp promoter, and then with PstI and HindIII. pFC11 (see below) was digested with PstI and HindIII to liberate the trp promoter and desired lac operator/linker fragment. These fragments were ligated under sticky-end conditions (3:1 molar ratio). The ligated DNA was digested with SacI to inactivate unwanted ligation products, and the mixture used to transform E. coli MM294. Successful transformants were selected for Amp®, LacO+ and Kan®, and plasmid DNA isolated. The correct construction of pFC20 was confirmed by restriction analysis. pFC20, as shown in FIG. 4, contains the desired linker/lac operator preceding the mtAPH-I 5' HindIII site, which is downstream from the trp promoter.

pFC11, used as the source of the polylinker/lacO sequences in pFC20, and ultimately as a source of the polylinker in pDG144, was constructed from pDG141 (supra) in two steps, the second of which is shown in FIG. 3:

pDG141 was first modified to convert a ClaI site at the 3' end of the trp promoter to a BamHI site by the conventional procedure, i.e., treatment of pDG141 with ClaI, blunt ending with Klenow, and blunt-end ligation with a commercial BamHI linker. The resulting ligation mixture was used to transform MM294 to Amp® and the presence of a BamHI site verified in the desired pFC10. pFC10 (FIG. 3) was digested with BamHI and ligated with BamHI digested pSYC111, (a 4.4 kb vector which had, in turn, been prepared by insertion of the desired 72 bp fragment into the BamHI site of pBR322; [This 72 bp fragment has the sequence: BamHI, SmaI, EcoRI, lacO, EcoRI, lacO, EcoRI, SmaI, BamHI.]). The ligation mixture was digested with PvuTT and used to transform MM294 to Amp®, LacO+ and screened for Tet$^S$. The correct construction of pFC11 was confirmed by restriction enzyme analysis.

D.2.a.2 Completion of pDG144

To obtain pDG144, pFC20 was treated as shown in FIG. 4. The trp promoter and lac operators were removed from pFC20 by digesting to completion with EcoRI, religating, and transforming MM294 to lacO$^-$ Kan$^S$. The correct construction, pDG144, contains the 22 bp polylinker bearing EcoRI, SmaI, and BamHI sites immediately upstream of the 5' HindIII site of mtAPH-I.

Digestion of pDG144 with HindIII and, respectively, StuI (when cloned in dcm$^-$ hosts) HaeII, coding sequence of the ∇2-10 Kan gene of 1.03, 1.08, MstI or PvuII yields DNA fragments containing the entire coding sequency of the □2-10 Kan gene of 1.03, 1.08, 1.15, or 1.21 kb. In these fragments, the ATG start codon is proximal to the 5' HindIII end.

D.2.b. Construction of pFC20* and pDG144*

Using the procedures set forth in ¶ K.2.a. above, but substituting for pFC19, pFC19*, the corresponding plasmids containing the mtAPH-I (∇2-9) coding sequence preceded by polylinker sequences are prepared.

D.3 Construction of Vectors with Alternative 5' Control Systems--pP$_L$Kan pP$_L$Kan contains the truncated ∇2-10 Kan gene under control of the P$_L$ promoter, a promoter which is regulated by a temperature sensitive repressor. The P$_L$ promoter in this plasmid can be removed as a EcoRI (or PstI)/HindIII P$_L$N$_{RBS}$ cassette.

To construct pP$_L$ Kan, the DNA sequence containing P$_L$ λ phage promoter and the ribosome binding site for the N-gene (N$_{RBS}$) is obtained from a derivative of pKC30 described by Shimatake and Rosenberg, *Nature* (1981) 292:128. pKC30 contains a 2.34 kb fragment from phage λ cloned into the HindIII/BamHI vector fragment from pBR322. The P$_L$ promoter and N$_{RBS}$ occupy a segment in pKC30 between a BglII and HpaI site. The derivative used as a source of the desired sequences has the BglII site converted to an EcoRI site as described below.

The BglII site immediately preceding the P$_L$ promoter was converted into an EcoRI site as follows: pKC30 was digested with BglII, repaired with Klenow and dNTPs and ligated with T4 ligase to an EcoRI linker (available from New England Biolabs) and transformed into *E. coli* K12 strain MM294 Lambda+. Plasmids were isolated from Amp ® transformants and the desired sequence confirmed by restriction analysis. The resulting plasmid, pFC3, was double-digested with PvuI and HpaI to obtain an approximately 540 bp fragment framing the desired sequence. This fragment was partially digested with HinfI and the 424 bp fragment isolated and treated with Klenow and dATP, followed by S1 nuclease, to generate a blunt-ended fragment with the 3' terminal sequence −AGGAGAA, where the −AGGAGA portion is the N$_{RBS}$. This fragment was restricted with EcoRI to give a 347 base pair DNA fragment with 5'-EcoRI (sticky) and HinfI(partial repair S1 blunt)-3' termini.

The truncated modified Kan gene is supplied by pDG144. pDG144 was digested with HindIII, blunt-ended with Klenow and dNTPs, and then digested with EcoRI. The vector fragment was ligated with the above-prepared EcoRI/HinfI(repaired) and transformed into MC1000-39531. Amp ® Kan ® (35° C.) colonies were selected, plasmids isolated and the correct sequence construction verified by restriction analysis and sequencing. One plasmid containing the correct sequence was designated pP$_L$Kan.

In a similar manner, but substituting other blunt-end promoter/RBS (procaryotes) or promoter (eucaryotes) sequences for those provided by pFC3 in this construction, similar plasmids to pP$_L$Kan may be constructed. Such constructions provide diagnostic systems for effectiveness of such 5' control sequences. Of course, pDG144* may also be substituted for pDG144 and used in this way.

The plasmids suitable for expression in eucaryotes described below were constructed using the restriction, modification and ligation techniques described in ¶ C.4. They are exemplary only; other plasmids which are replicable in eucaryotes, which contain the mtAPH-I coding sequence operably linked to control sequences suitable to eucaryotes, and which contain restriction sites suitable for insertion of foreign desired DNA expression cassettes or for insertion of the promoter and N-terminal coding sequences for production of fusion proteins can be constructed using these techniques as is understood by those skilled in the art.

Further, the plasmids described below can be used as starting materials and modified by substituting alternate control sequences and replicons chosen from those appropriate to the desired host, as is understood by those skilled in the art and as is illustrated in ¶ D.8. An illustrative list of such sequences is set forth in ¶ C.1. In addition, the mtAPH-I ∇2-10 sequences can, if desired, be excised and replaced by the corresponding ∇2-9 sequences from pDG144* or pFC20*, or by other mtAPH-I sequences.

D.4. Deposited Vectors and Derivatives with Eucaryotic Control Sequences

Figure 7:
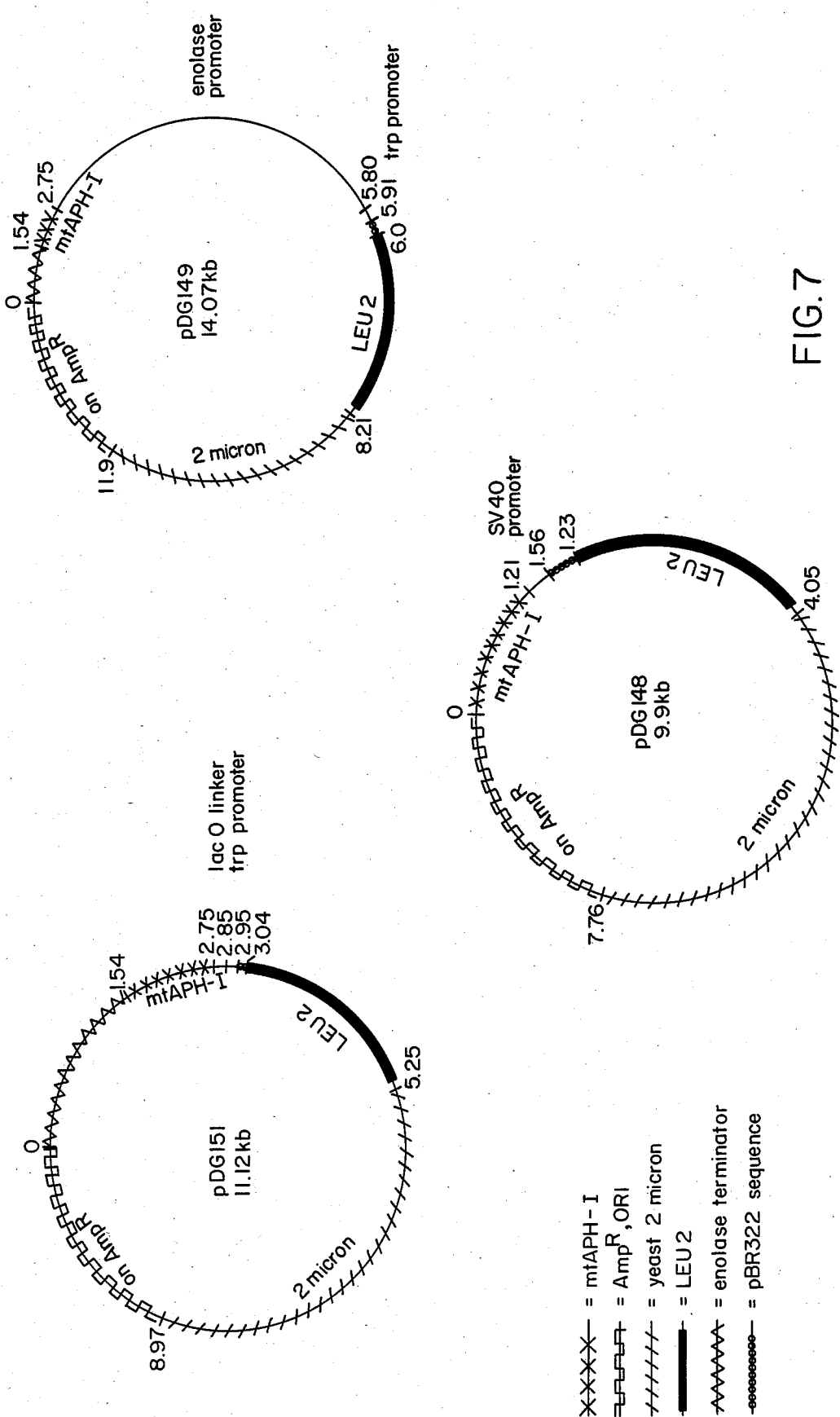
FIG. 7 shows, schematically, the features of pDG148, pDG149 and pDG151.

D.4.a. pDG148 SV40 Control)

pDG148, diagrammed in FIG. 7, contains the truncated ∇2-10 Kan gene under control of the SV40 promoter. This plasmid is illustrative of vectors suitable for expression of the Kan gene in eucaryotic cells and as a host plasmid for eucaryotic foreign gene expression providing mtAPH-I as a dominant selectable marker. It is also usable as a host plasmid providing the mtAPH-I C-terminal sequences of the fusion flag. pDG148 will replicate autonomously both in procaryotic (e.g., *E. coli*) and in eucaryotic cells (e.g., yeast and certain mammalian cell line) hosts. pDG148 was deposited with ATCC on Dec. 22, 1983, and was given accession number 20695. The sequences in pDG148 (with reference to FIG. 7) are as follows:

1. The 1.21 kb fragment comprising the first 1.21 kb of pDG148 is the HindIII/PvuII modified truncated Kan gene cassette from pDG144. This sequence, as stated above, has been mutated at codons 93/94 (of the truncated gene) to eliminate the XmaI/SmaI recognition site and at codons 175/176 to destroy the HindIII recognition site while retaining the same amino acid sequence in the encoded protein.

2. The SV40 viral promoter sequence containing the SV40 origin of replication, early viral promoter and transcriptional enhancer, is obtained by digesting isolated SV40 DNA with HindIII and PvuII and ligating the blunt-ended PvuII end to a BamHI linker obtained from New England Biolabs. This occupies coordinates 1.21-1.56.

3. Coordinates 1.56 kb to 1.83 kb are a 276 bp DNA fragment from pBR322 obtained by double digestion with BamHI and SalI and isolation of the 276 bp fragment.

4. The LEU2 gene from yeast occupies coordinates 1.83 kb-4.05 kb. This is derived from pYE13 (Broach, J., et al, Gene (1979) 8:121) by double digestion of this plasmid with XhoI/SalI.

5. A yeast replication origin derived from the yeast 2 micron plasmid occupies coordinates 4.05 kb-7.76 kb. It is obtained by digestion of pDB248 (Beach, D., et al, Nature (1981) 290:140) with EcoRI(repair)/SalI and isolation of the 3.7 kb DNA fragment containing the replicon. The existence of the appropriate SalI site was not deducible from the disclosure of Beach. However, pDB248 was shown to contain a SalI site about 50 bp downstream from te indicated LEU2 region/2μ PstI tailing site as set forth in the Beach reference.

6. Finally, this plasmid is capable of replication in *E. coli* and of conferring Amp resistance by inclusion of a 2145 bp DNA fragment obtained from pBR322 by double digestion with TthlllI(repair) and EcoRI. It occupies coordinates 7.76kb-9.9 kb of the 9.9 kb pDG148.

D.4.b. pDG149 (Enolase Control)

pDG149, diagrammed in FIG. 7, is similar to pDG148 except that the truncated Kan gene (∇2-10) is under the control of the enolase promoter and terminator rather than the SV40 promoter. The plasmid retains the yeast replicative sequences, the LEU2 gene, and the Amp® and *E. coli* origin of replication derived from pBR322. pDG149 was deposited with ATCC on December 22, 1983, and given accession number 20694. The segments of pDG149 are as follows:

1. Coordinates 0-1.54 kb contain 3' untranslated ENO1 yeast gene terminator sequences and are derived from a HindIII(repaired)/EcoRI digest of peno46 (Holland, M. J., et al, *J Biol Chem* (1981) 256:1385). The resulting EcoRI site is at coordinate 0, and the blunt-end segment of the ENO1 fragment is ligated to the modified truncated Kan gene described below.

2. Coordinates 1.54-2.75 kb contain the truncated Kan gene modified as set forth in connection with pDG148 above and also obtained from pDG144 digested with HindIII and PvuII. The PvuII site at the 3' end of the gene is ligated to the HindIII, repaired, blunt end of the enolase terminator thus leaving a unique HindIII site (5' to mtAPH-I) for subsequent ligation.

3. The enolase I promoter which is contained in the coordinates 2.75-5.80 kb was obtained from two intermediate derivatives of peno46 (Holland, M. J., et al, supra). The first intermediate was obtained by digestion with HindIII, limited treatment with *E. coli* exonulcease III, S1 nuclease and insertion of a SalI linker obtained from New England Biolabs. The resultant intermdeiate vector was treated with SalI, repaired with Klenow, and ligated with a HindIII linker obtained from New England Biolabs. This second modification placed a HindIII site preceding the ATG initiation codon for the enolase I protein. This second intermediate derivative plasmid was double digested with XmaI and HindIII to provide the 3.05 kb fragment which contains 1.76 kb of yeast DNA and also contains 1.29 kb of ColEl plasmid DNA encoding a portion of the colicin E1 protein.

4. Coordinates 5.80-5.91 kb contain the 112 bp trp control DNA fragment which was obtained by double digestion of pFC11 (¶D.2.a.1) with EcoRI, repair with Klenow, followed by digestion with XmaI and isolation of the 112 bp fragment having EcoRI (blunt) at the 5' coordinate (5.91 kb) and XmaI at the 3' coordinate (5.8 kb).

5. A 90 bp linking segment which comprises the DNA fragment between the SphI(repair) and SalI recognition sites of pBR322 occupies coordinates 5.9-6.0.

6. The LEU2 gene derived from yeast as a XhoI/SalI fragment occupies coordinates 6.0-8.21. This fragment was obtained in the same manner as that used to construct pDG148.

7. The 3.7 kb DNA fragment containing the 2 micron origin of replication for yeast was derived from pDB248 as described for pDG148 and occupies coordinates 8.21 to 11.93.

8. The Amp® gene and *E. coli* replication origin occupying coordinates 11.93-14.07 kb were derived from pBR322 as a TthlllI(repair)/EcoRI fragment as described above.

D.4.c. pDG150 (Enolase Control)

pDG150 was derived from pDG149 by deleting extraneous sequences of bacterial origin upstream of the enolase promoter, i.e., the trp promoter and the Colicin E1 sequences brought along with the peno46-derived fragment.

pDG149 was cut with SalI (complete) at the unique Sal site upstream of the trp promoter sequence, and then subjected to partial digestion with XbaI to obtain cleavage at the Xba site immediately 5' of the yeast derived enolase promoter. After repair with Klenow and the four dNTPs, the mixture was ligated and used to transform *E. coli* MM294 to Amp®. The transformants were screened for the desired 11.62 kb plasmid containing unique XbaI and SalI sites. (The SalI site is regenerated upon ligation, the XbaI site is not.) The correct construction wasdesignated pDG150.

D.5 Preparation of Vectors Suitable for Fusion

Flag Construction--pDG151 pDG151 is a 11.12 kb plasmid analogous to the foregoing pDG148, pDG149 and pDG150, except that the modified truncated Kan gene is linked to additional procaryotic control systems comprising duplicated lac operators in front of the trp promoter of pDG149 and is preceded by a polylinker. The eucaryotic promoter sequences linked to mtAPH-I have been deleted. In pDG151, the ENO1 control sequences intervening between the trp promoter and the ∇2-10 modified Kan gene from pDG149 are replaced by a 0.1 kb sequence containing a duplicated lac operator flanked by a short inverted repeat polylinker, and expression of the mtAPH-I can thus be regulated by either tryptophan levels or lac repressor synthesis. This fragment was derived by HindIII/BamHI(partial) digestion of pFC20 (see ¶D.2.a.1).

The sequences of pDG151 are outlined in FIG. 7, and consist of the following:

1. Coordinates 0-1.54 are the 1.54 kb HindIII/EcoRI 3' untranslated terminator sequences of the Eno1 gene derived from peno46 (Holland, et al, supra) and are identical with the sequences in the corresponding coordinates in pDG149.

2. Coordinates 1.54-2.75 contain the truncated Kan gene modified as noted above. This is the same HindIII/PvuII digest of pDG144 described in connection with the corresponding sequences in pDG149, and which corresponds to the sequence occupied by coordinates 0-1.21 in pDG148.

3. Coordinates 2.75-2.85 contain the duplicated lac operator sequence flanked by inverted polylinker repeats and was obtained from pFC20 (see FIG. 4) by digestion with HindIII and BamHI(partial). Correct BamHI digestion to give the fragment which includes the lacO was readily verified by transforming hosts to Amp® and then screening for consititutive LacZ+ expression in *E. coli* K12 strain MMZ94. The sequence immediately preceding the ATG start codon (at 2.75) is:

5' G AAT TCC  CGG  GGA TCC GGC GAT AAG CTT ATG
    EcoRI      XmaI  BamHI          HindIII 4. Coordinates 2.85-2.95 are the isolated 107 bp 5'-EcoRI(repaired)/BamHI-3' fragment from pFC10. This fragment contains the trp promoter-operator and is analogous to the 112 bp trp control fragment which occupies coordinates 5.80-5.91 kb in pDG149.

5. Coordinates 2.95-3.04 kb contain a 90 bp pBR322 segment between the SphI(repair) and SalI sites.

6. The LEU-2 gene from YEp13 occupies coordinates 3.04-5.25. It was obtained as a XhoI/SalI digest from YEp13 and is the same fragment as that which occupies similar locations in pDG148 and pDG149.

7. The 2 micron plasmid replicon in coordinates 5.25-8.97 is analogous to the pDB248 derived fragments in pDG148 and pDG149.

8. Coordinates 8.97-11.2 contain a Tth111I/EcoRI th digest of pBR322 which supplies Amp® and an *E. coli* origin of replication.

As pDG151 contains a polylinker preceding the ATG start of mtAPH-I, convenient restriction sites for creation of 5' fusion termini are available.

D.6 Construction of Expression Vectors for LEU2mtAPH-I Fusions

Four expression vectors were constructed which are effective in the production of LEU2fusion proteins in yeast host. These fusion proteins contain the N-terminal sequences of β-isopropyl malate in varying lengths, a few linker encoded amino acids, and the mtAPH-I sequence. All four such plasmids constructed were derived from pDG151 by cutting into the LEU2 sequence contained between coordinates 3.04 and 5.25 at various positions in the coding region and religating the N-terminal portion of the coding sequence into a polylinker which immediately precedes the mtAPH-I coding sequences in pDG151. These illustrative plasmids were designated pLK11.17, pLK51.57, pLK82.88, and pLK82.90. The designations refer to the coding sequences which make up the fusion (L (LEU) and K (Kan)) and to the nature of the fusion, the first number referring to the number of codons of the LEU2 sequence included, and the second number referring to the number of additional amino acids preceding the start codon for mtAPH-I.

As described in paragraph D.5, the polylinker immediately preceding the mtAPH-I coding sequence contains four restriction sites: EcoRI, SmaI, BamHI, and HindIII. The LEU2 coding sequence contains a BstEII site which cuts at codons 12-14, a ClaI site which cuts at codons 51-52, and a KpnI site which cuts at codons 83-84. The following subparagraphs detail the use of these sites in the construction of exemplary fusion protein encoding plasmids.

D.6.a. Construction of pLK11.17 pDG151 was digested to completion with BstEII, treated with SI nuclease, digested with PstI, and the 5.8 kb DNA fragment was purified following agarose gel electrophoresis. The BstEII LEU2 site is as shown:

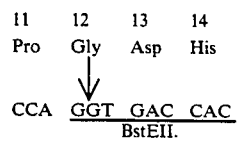

This 5.8 kb fragment sequences and the first 11 codons of the LEU2 sequence and the first nucleotide of codon 12.

To provide the mtAPH-I portion, the pDG151 was digested to completion with BamHI, treated with Klenow in the presence of all four dNTPs, digested with PstI, and the 3.52 kb DNA fragment purified. This fragment provides the coding sequence for mtAPH-I, along with codons for 52/3 amino acids encoded by the polylinker, and also provides the enolase termination sequences.

Equimolar mixtures of the above pDG151 fragments were ligated at a total DNA concentration of 60 μg/ml under sticky-end conditions for 12 hours and then under blunt-end conditions at a DNA concentration of 20 μg/ml. The ligation mixture was used to transform *E. coli* MM294 to Amp®, and the Amp® colonies screened for the presence of the desired 9.3 kb plasmid, which was expected to contain a unique regenerated BamHI site.

Candidate plasmids were further screened by restriction enzyme analysis, and then by DNA sequencing using a pentadecamer primer 5' CAGCATC-CATGTTGG-3' which is complementary to nucleotides 23-37 of the mtAPH-I coding sequence. The nucleotide sequence at the fusion was confirmed to be:

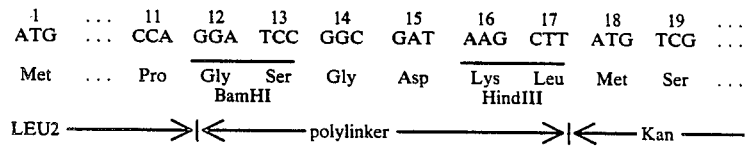

D.6.b. Construction of pLK51.57 pDG151 was digested to completion with ClaI, treated with Klenow in the presence of dCTP and dGTP, digested with PstI, and the 5.92 kb DNA fragment was isolated. ClaI cleaves the LEU2 coding sequence as shown:

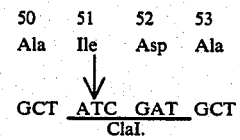

```
        50   51   52   53
        Ala  Ile  Asp  Ala
             ↓
        GCT ATC GAT GCT
            ─────────
              ClaI.
```

This fragment thus provides, in addition to the LEU2 promoter, codons 1-51 of the LEU2 sequence along with the first nucleotide of codon 52.

The 5.92 kb fragment containing the mtAPH-I codons and enolase terminator was prepared exactly as set forth in paragraph D.6.a above.

Equimolar amounts of these fragments were ligated and the ligation mixture used to transform *E. coli* MM294 to Amp ® as described in paragraph D.6.a above. Amp ® colonies were screened for the desired 9.44 kb plasmid containing the unique regenerated BamHI site. Candidate plasmids were further screened by restriction analysis. DNA sequencing using the same pentadecamer primer as above confirmed the sequence at the fusion of the correct construction, pLK51.57 to be:

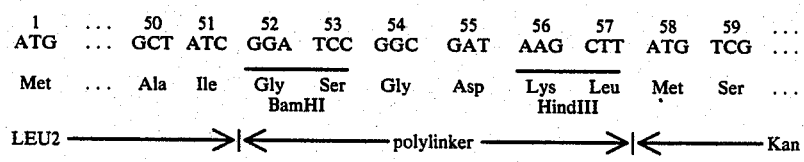

```
1        50   51   52   53   54   55   56   57   58   59
ATG ...  GCT  ATC  GGA  TCC  GGC  GAT  AAG  CTT  ATG  TCG ...

Met ...  Ala  Ile  Gly  Ser  Gly  Asp  Lys  Leu  Met  Ser ...
                   BamHI              HindIII LEU2 ─────>|<──── polylinker ────>|<──── Kan
```

D.6.c. Construction of pLK82.88 pDG151 was digested to completion with KpnI, digested with BamHI, and treated with Klenow in the presence of all four dNTPs. KpnI cleaves the LEU sequence as shown:

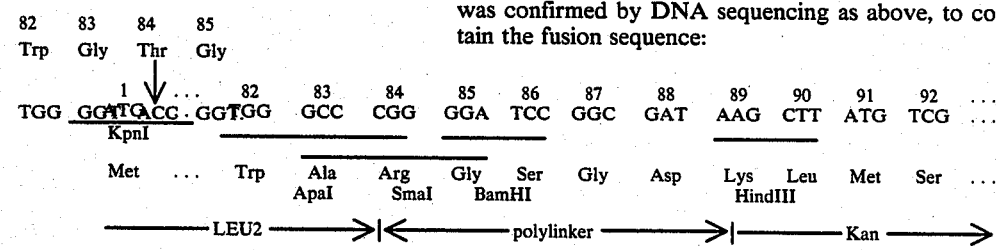

```
         82   83   84   85
         Trp  Gly  Thr  Gly
                   ↓
              1  ↓...   82   83   84   85   86   87   88   89   90   91   92
         TGG GGTACC  GGTGG GCC  CGG  GGA  TCC  GGC  GAT  AAG  CTT  ATG  TCG ...
             ─────
             KpnI

Met ... Trp  Ala  Arg  Gly  Ser  Gly  Asp  Lys  Leu  Met  Ser ...
                      ApaI SmaI BamHI          HindIII ───── LEU2 ────>|<──── polylinker ────>|──── Kan ───>
```

Thus, the resulting linear blunt-ended fragment contains at the KpnI (blunt) end the LEU2 promoter along with the first 82 codons of the LEU2 gene, and an additional G from codon 83; the BamHI (blunt) end provides the codons for mtAPH-I, preceded by several polylinker codons, and followed by the enolase terminator.

The fragments were ligated under blunt-end conditions at a total DNA concentration of 2μg/ml to favor intramolecular blunt-end ligation, and the mixture used to transform MM294 to Amp ®. Amp ® colonies were screened for the presence of the desired 9.54 kb plasmid containing the unique regenerated BamHI site. Candidate plasmids were further mappe by restriction analysis and finally by DNA sequencing. The relevant fusion sequences in pLK82.88 were confirmed to be:

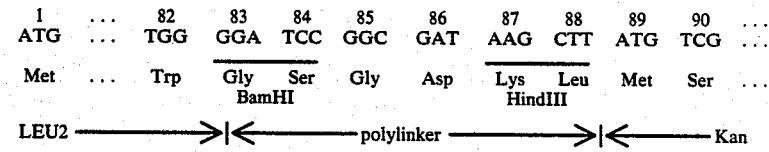

```
1        82    83   84   85   86   87   88   89   90
ATG ...  TGG   GGA  TCC  GGC  GAT  AAG  CTT  ATG  TCG ...

Met ...  Trp   Gly  Ser  Gly  Asp  Lys  Leu  Met  Ser ...
               BamHI              HindIII LEU2 ─────>|<──── polylinker ────>|<──── Kan
```

D.6.c. Constructed of pLK82.90 pDG151 was digested to completion with KpnI, blunt-ended with Klenow in the presence of dGTP, digested with BglII and the desired 6.88 kb DNA fragment was purified. This fragment provides the LEU2 promoter, the first 82 LEU2 codons, and 1 nucleotide of codon 83. To obtain the Kan gene for fusion, pDG151 was digested to completion with EcoRI, treated with S1 nuclease, digested with BglII, and the desired 2.53 kb fragment purified. This fragment provides 7 ⅔ codons from the polylinker.

The 2 foregoing fragments were ligated in equimolar ratio under sticky-end conditions (60 μg/ml total DNA), diluted to 10 μg/ml and ligated under bluntend conditions to favor intramolecular ligation. The ligation mixture was transformed into *E. coli* MM294 to Amp ® and the colonies screened for the presence of the desired 9.4 kb plasmids containing an additional ApaI recognition site. Plasmids were further mapped by restriction analysis and the correct construct, pLK82.90, was confirmed by DNA sequencing as above, to contain the fusion sequence:

D.7 Construction of Plasmids Containing Enolase Fusions pEK7.14 encodes inframe fusions of the first 7 codons of EnO1, 7 codons of polylinker, and the 262 mtAPH-I codons, all under the control of the enolase promoter and terminating sequences. The mtAPH-I codons and enolase terminator are derived from pDG151; the remaining codons and enolase promoter are obtained from a derivative of peno46.

To obtain the derivative, peno46 was first modified by digesting with HindIII, treating with *E. coli* exonucleaseIII, S1 nuclease, BAP and ligation in the presence of the self-complementary phosphorylated SalI octanucleotide 5'-GGTCGACC-3' under blunt-end conditions. The ligation mixture was used to transform *E. coli* MM294 t Amp®, and Amp® colonies screened for the presence of a new SalI site. The modified plasmid, peno46(I24) was confirmed by dideoxy sequencing to have inserted the SalI octanucleotide immediately after codon 7 in the Eno1 coding sequence. This SalI cleavage site is -1 in the Eno1 reading frame and encodes a Gly-Arg-Pro tripeptide.

The desired sequences from peno46(I24) were transferred to M13 phage to provide M13mp8::Eno46(I24). To do this, peno46(I24)- was digested with SalI and EcoRI, and the desired 745 bp ENO1 promoter fragment purified. Bacteriophage M13mp8RF DNA was digested to completion with EcoRI and SalI and the above purified 745 bp fragment and the M13 vector were ligated (3:1 molar ratio) at 50 µg/ml total DNA concentration under sticky-end conditions. *E. coli* K12 strain WB373 (an M13-sensitive host) was transformed with 100 nanograms of the ligation mixture, and the plaques screened for the presence of the 745 bp insertion. The desired recombinant phage fuses 7 codons of he polylinker sequence from M13mp8 in frame to the first 7 codons of Eno1 provided by peno46(I24). The reading frame encoded by the HindIII site in this recombinant phage is identical (+1) with the reading frame encoded by the polylinker HindIII site (+1) in pDG151. Thus, this recombinant phage is a convenient source for the 760 bp EcoRI/HindIII fragment used to construct pEK7.14.

The recombinant phage, M13mp8Eno46(I24) RF DNA, was digested with EcoRI, repaired with Klenow in the presence of dATP and TTP, digested with HindIII, and the 760 bp ENOI promoter fragment purified. Plasmid pDG151 was digested to completion with SalI, repaired with Klenow in the presence of all four dNTPs, and digested with HindIII. The purified ENO1 promoter and digested vector fragments were ligated in a 2:1 molar ratio under sticky-end conditions at 60 µg/ml total DNA, and the ligated fragments diluted to 20 µg/ml and ligated under blunt-end conditions. The mixture was used to transform *E. coli* MM294 to Amp® on plates containing X-gal, and white Amp® transformants were screened for the presence of the desired 11.6 kb plasmid. (Transformants containing plasmids which had deleted the 280 bp lac operator fragment preceding mtAPH-I would be expected to give white colonies.)

Candidate plasmids were further mapped by restriction enzyme digestion and the resulting sequence at the fusion confirmed in pEK7.14 to be:

D.8 Construction of pDG151::RSV; a Vector Having Alternative Control Sequences pDG151:RSV is a *S. cerevisiae/E. coli* vector using control sequences derived from Rous Sarcoma Virus. It is constructed from pDG151 by removing the sequences between coordinates 3.04 and 2.75 and replacing them with the RSV promoter sequences (religation at the ATG-preceding HindIII site regenerates operable linkage of the promoter with the mtAPH-I codons).

Plasmid pDG151 was digested to completion with SalI, treated with *E. coli* DNA polymerase I, Klenow fragment, in the presence of all four dNTPs, and finally digested to completion with HindIII. Plasmid pRSV-NeoI (see below) was digested to completion with NruI and HindIII. The digested DNA fragments were mixed (1:2.5 molar ratio) and ligated at 50 µg/ml (total DNA concentration) under sticky-end conditions. The ligated linear DNA fragments were diluted to 25 µg/ml and further ligated under blunt-end conditions to favor intramolecular circle formation. The ligated DNA was digested with PvuII (to inactivate undesired pRSV-NeoI ligation products) and 150 ng of the DNA used to transform *E. coli* K12 strain MM294 to amplicillin resistance. Non-constitutive Lac+ colonies (absence of 280 bp SalI/HindIII DNA fragment of pDG15) were screened for kanamycin resistance. Amp®Kan® candidate colonies were screened for the presence of the desired 11.24 kb plasmid containing the 400 bp NruI/HindIII DNA fragment encoding the Rous Sarcoma virus promoter. Plasmid pDG151::RSV (11.24 kb) released the diagnostic 1235 bp EcoRI fragment (fusion of 928 bp of LEU2 DNA to 307 bp of RSV DNA), regenerated the desired SalI recognition site (SalI repair, GTCGA/CGA, NruI fusion) and generated the diagnostic SalI/EcoRI (307 bp) and NruI/EcoRI (150 bp) DNA fragments.

D.8.1 Construction of pRSVNeoI

Plasmid pRSVneo (5.73 kb, renamed here pRSVneoII to distinguish the APH-II coding sequence from the modified, truncated APH-I coding sequence of this invention) as been described (Gorman, C., et al, *Science* (1983) 221:551-553). pRSVneoII was modified to give pRSVNeoI by replacing the 1210 bp HindIII/PvuII DNA fragment encoding the mtAPH-I coding sequence (from plasmid pFC20) for the 1352 bp HindIII/PvuII region of pRSVneoII encoding the bacterial promoter and structural coding sequences for APH-II (Beck, E., et al, *Gene* (1982) 19;327).

Plasmid pRSVneoII was digested to completion with PvuII and HindIII Plasmid pFC20 was digested to completion wth PvuII and HindIII. The digested DNA fragments were mixed (1:1 molar atio) and ligated at 40 µg/ml (total DNA concentration) under sticky-end conditions. The ligated linear DNA fragments were diluted to 20 µg/ml and further ligated under blunt-end conditions to favor intramolecular circle formation. *E. coli* K12 strain MM294 was transformed to Amp®

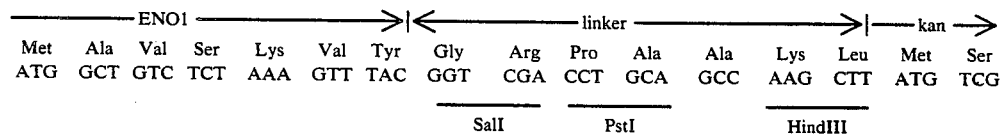

with 150 ng of the ligated DNA and non-constitutive Lac+colonies (transformed with the pRSVneoII origin containing fragment rather than the pFC20 origin containing fragment) were screened for the presence of the desired 5.59 kb plasmid. Plasmid candidates were screened with HindIII (unique site), PvuII (unique site), HindIII/PvuII (4.3 and 1.21 kb DNA fragments), and EcoRI (3.04 and 2.55 kb DNA fragments). Plasmid DNA from one transformant, designated pRSVneoI (5.59 kb), encoded the mtAPH-I codin sequence substituted for the APH-II promoter and coding sequence. Additionally, plasmid pRSVneoI conferred a high level of kanamycin resistance to E. coli K12 strain MM294 (22100bbbKg/ml).

E. Expression of Truncated Kan Gene

E.1 Expression in E. coli

FIG. 5 indicates that plasmid MCK 4.1 has lost codons ∇2-10 of the wild type APH-I protein (∇2-10) yet confers a very high level of resistance kanamycin (100% plating efficiency at 300 µg/ml drug) on minimal media. Similarly, plasmid MCK 1.4 has lost codons 2-9 of the wild type APH-I protein and confers a very high level of resistance to kanamycin. Thus the cysteine at position 10 in the wild-type sequence and amino acids 2 through 9 of the wild-type protein sequence are not essential for activity.

Figure 6:
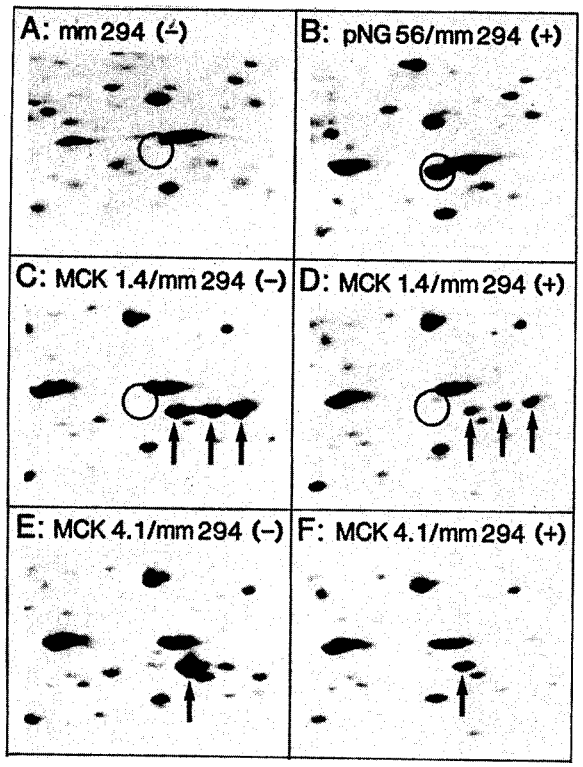
FIG. 6 shows the results of 2-D electrophoretic analysis of protein extracts of E.coli transformed with pNG56, pMCK4.1 and pMCK1.4.

FIG. 6 shows a portion of a series of two dimensional electrophoretic separations (O'Farrell, P. J., et al, *J Biol Chem* (1975) 250:4007) of extracts from E. coli K12 strain MM294 harboring no plasmid (Panel A), wild-type plasmid pNG56 (Panel B), plasmid MCK 1.4 (codon 2-9 deletion) (Panels C and D) or plasmid MCK 4.1 (codon 2-10 deletion) (Panels E and F). Cultures were grown in the absence (Panels A, C, E) or presence (Panels B, D, F) of tryptphan (100 µg/ml) and labeled with 35S-Methionine (10 µc/ml) for five minutes.

FIG. 6 demonstrates that plasmids MCK 4.1 and MCK 1.4 encode proteins of lower apparent molecular weight and altered apparent charge. Compare position of circled wild-type protein (Panel B) with arrows indicating new polypeptide chains synthesized by cells harboring plasmids MCK 1.4 and MCK 4.1. In addition, FIG. 6 demonstrates that the synthesis of these new, altered polypeptides is regulated by the level of tryptophan in the medium (cf panels C and E with D and F, respectively) consistent with the truncated coding sequences of this mixture in operable linkage to the E. coli trp promoter. Furthermore, purified APH-I∇2-10 comigrates with the new, major labeled spot indicated in panel E (not shown).

Further, the altered HindIII recognition site mutation encoded by plasmid pFC15 and the altered XmaI/SmaI recognition site encoded by plasmid pFC19 do not change the high level of resistance conferred by these modified APH-I coding sequences.

E.2 Expression in Eucaryotes

Use of mtAPH-I as a Dominant Selectable Marker, or Fusion Flag

The efficacy of mtAPH-I as a selection tool for eucaryotic transformation is shown by the results in Table 1.

TABLE 1

| Plasmid | Promoter | Transformation Frequency 100 µg G418/ml | 200 µg G418/ml |
|---|---|---|---|
| pDG150 | ENO1 | $1.2 \times 10^3$ | $0.18 \times 10^3$ |
| pLK11.17 | LEU2 | $1.3 \times 10^3$ | $0.98 \times 10^3$ |
| pDG148 | SV40 early | $0.5 \times 10^3$ | $0.12 \times 10^3$ |
| pDG151::RSV | Rous LTR | $1.2 \times 10^3$ | $0.83 \times 10^3$ |

Plasmids encoding mtAPH operably linked to control sequences appropriate to eucaryotes were used to transform S. Cerevisiae S173-6B protoplasts as described. As shown in Table 1 transformation frequencies of the expected magnitude were obtained. Frequencies are expressed as directly selected S418 ® transformants/µg of plasmid DNA.

Figure 8:
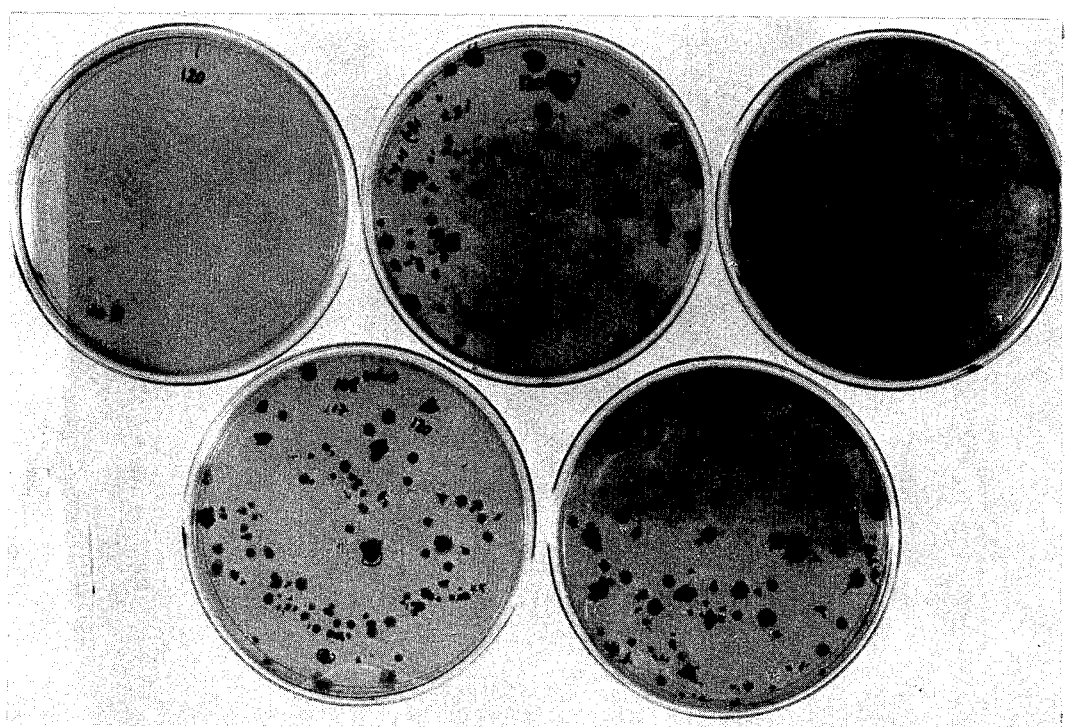
FIG. 8 shows the results of G418 direct selection of a laboratory yeast strain transformed with various mtAPH-I expression plasmids.

The results of Table I are also shown in FIG. 8 which compares growth on G418 containing medium of both transformed and non-transformed S173-6B: (1) no plasmid; (2) pLK11.17; (3) pDG148; (4) pDG150; (5) pDG151::RSV.

The transformation frequencies selected by G418 were 2-4 fold higher than those obtained using LEU2+selection.

Figure 9:
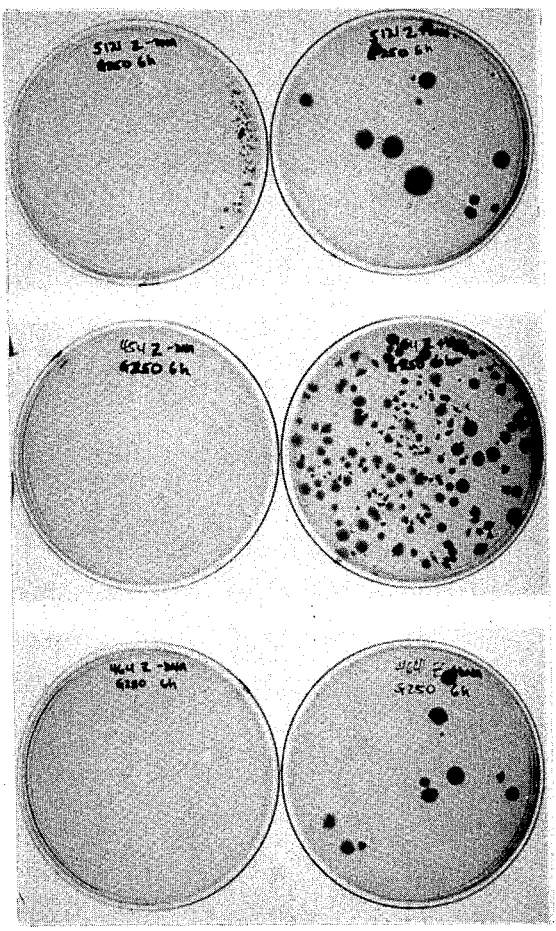
FIG. 9 shows the results of G418 direct selection of industrial yeast strains transformed with pDG149 mtAPH-I expression plasmid.

FIG. 9 shows similar results obtained when the hosts were industrial yeast strains. S.cerevisiae strains 5121, C454, C464, three industrial yeast strains used for ethanol production or the baking of bread, Red Star, CBS6508, and GB4722, were transformed with plasmid pDG149 and the transformants directly selected for G418 ® as described in ¶ C.3. The plates on the left resulted from G418 ® selection of protoplasts not treated with plasmid DNA. In contrast, the plates on the right resulted from G418 ® selection of protoplasts treated with pDG149. The top panel is Red Star; the middle panel is CBS6508; the bottom panel is GB4722.

Southern blots of DNA extracted from transformed yeast performed according to the procedure of ¶ C.7, further confirmed the presence of the mtAPH-I coding sequence in the transformed hosts.

E.3 Resistance Levels Obtained

The level of G418 resistance conferred on yeast by plasmids containing eucaryotic control systems is even greater than the level of Kan ® conferred on E. coli by plasmids containing the trp promoter or LEU2 promoter, both operable in E. coli.

Table 2 shows the concentrations of antibiotic required to give a 50% plating efficiency for plasmid-containing cells. The column designated "E. coli" shows kanamycin resistance for plasmid-containing E. coli K12 strain MM294; the column designated "S. cerevisiae" shows G418 resistance for plasmid containing S. cerevisiae strain S173-6B.

TABLE 2

| | Host | |
|---|---|---|
| Plasmid | E. coli | S. cerevisiae |
| None | <5 µg/ml | <25 µg/ml |
| pDG148 | <5 µg/ml | 160 µg/ml |
| pDG149 | <5 µg/ml | >1.0 mg/ml |
| pDG150 | <5 µg/ml | >1.0 mg/ml |
| pFC19 | >150 µg/ml | N.D. |
| pDG151::RSV | >100 µg/ml | 500 µg/ml |
| pLK11.17 | 10 µg/ml | >1.0 mg/ml |
| pLK51.57 | >300 µg/ml | >1.0 mg/ml |
| pLK82.88 | >300 µg/ml | >1.0 mg/ml |
| pLK82.90 | >300 µg/ml | >1.0 mg/ml |

The following plasmids have been deposited at the American Type Culture Collection, Rockville, Maryland, U.S.A. (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers. The plasmids have also been deposited with the Master Culture Collection (CMCC) of Cetus Corporation, Emeryville, Calif., U.S.A., the assignee of the present application, and assigned the indicated CMCC deposit numbers:

| Plasmid | CMCC Deposit No. | ATCC No. |
| --- | --- | --- |
| pDG144 | 1960 | 39579 |
| pFC19 | 1832 | 39551 |
| pDG149 | 1928 | 20694 |
| pDG148 | 1929 | 20695 |
| pDG141 | 1966 | 39588 |

We claim:

1. A DNA sequence cassette encoding a dominant selectable marker effective in procaryotic and in eucaryotic transformants which comprises:
   an ATG start codon in reading frame with the codons of a modified truncated aminoglycoside phosphotransferase-I (APH-I) gene, designated herein mtAPH-I, and at least one cassette-unique restriction site upstream of and proximal to the ATG start codon,
   said mtAPH-I defined herein as the coding sequence for APH-I modified so as to retain the amino acid sequence encoded by the APH-I gene, but to eliminate any restriction site otherwise duplicative of said cassette-unique restriction site, and truncated by deletion of codons encoding at least one amino acid in positions 2-10 inclusive.

2. The DNA sequence cassette of claim 1 wherein the cassette-unique restriction side is selected from the group consisting of HindIII, BamHI, XmaI, SmaI, and EcoRI.

3. The DNA sequency cassette of claim 2 wherein the cassette-unique restriction site is HindIII.

4. A recombinant expression vector that confers resistance to G418 on a procaryotic or eucaryotic transformant wherein said vector comprises an ATG start codon in reading frame with the codons of the mtAPH-I gene of claim 1 wherein the ATG codon and the codons of said mTAPH-I gene are operably linked to appropriate control sequence operable in the transformant host.

5. The vector of claim 4 which confers resistance to G418 on a bacterial host and wherein the control sequences comprise the trip promoter.

6. The vector of claim 5 which is selected from the group consisting of pFC19, pFC20, and pDG151.

7. The vector of claim 4 which confers G418 resistance on a bacterial host and wherin the control sequences comprise the P$_L$ promoter.

8. The vector of claim 7 which is pPL Kan.

9. The vector of claim 4 which confers G418 resistance on a eucaryotic cell wherein the control sequences comprise a promoter functions for eucaryotic cells.

10. The vector of claim 9 wherein the promoter is selected from the group consisting of the Sv40 early promoter, RSV promoter and yeast enolase promoter.

11. The vector of claim 10 which is selected from the group consisting of PDG148, pDG149, pDG150, and pDG151::RSV.

12. A vector capable, when provided functional control sequences, of conferring G418 resistance on a eucaryotic cell wherein said vector comprises the DNA sequence of claim 1 operably linked to a polyadenylation signal and provided with 5' flanking restriction sites to permit insertion of a promoter and codnons for an N-terminal fusion sequence.

13. The vetor of claim 12 which is pDG151.

14. Recombinant host cells transformed with a a vector containing the portable DNA sequence of claim 1.

15. Recombinant host cells transformed with the vector of claim 4.

16. Recombinant host cells transformed with the vector of claim 12.

17. An expression vector, operable in eucaryotic host cells, which comprises the mtAPH-I coding sequences of claim 1 operably linked to control sequences appropriate to the eucaryotic host.

18. The vector of claim 17 which further includes the coding sequence for at least one peptide operably linked to control sequences competent to effect its expression in the eucaryotic host.

19. An expression vector, operable in eucaryotic host cells, which comprises the coding sequence for a fusion protein operably linked to control sequences functional in an eucaryotic host wherein the encoded fusion protein comprises a desired peptide as the N-terminal sequence and mtAPH-I of claim 1 as the C-terminal sequence.

20. The vector of claim 19 wherein the control sequnces comprise the promoter endogenous to the N-terminal sequence of the fusion protein.

21. The vector of claim 20 wherein the N-terminal sequence comprises at least 10 amino acids of the amino acid sequence of β-isopropylmalate dehydrogenase.

22. The vector claim 20 wherein the N-terminal sequence comprises at least the first seven amino acids of the N-terminal sequence of yeast enolase.

23. Recombinant host cells transformed with the vector of claim 18.

24. Recombinant host cells transformed with the vector of claim 19.

25. A method of selecting eucaryotic cells which have been transformed with the vector of claim 4 which comprises plating a suspension of said cells on medium containing the antibiotic G418, and selecting colonies which are resistant to G418.

26. A method of selecting eucaryotic cells which have been transformed with the vector of claim 17 which comprises plating a suspension of said cells on medium containing the antibiotic G418, and selecting colonies which are resistant to G418.

27. A method of selecting eucaryotic cells which have been transformed with the vector of claim 19 which comprises plating a suspension of said cells on medium containing the antibiotic G418, and selecting colonies whioh are resistant to G418.

28. A method of producing a protein which comprises culturing cells which have been selected by plating a suspension of cells which have been treated with the vector of claim 18 on medium containing the antibiotic G418, and selecting colonies which are resistant to G418.

29. A method of producing fusion proteins which comprises culturing cells transformed with the expression vector of claim 19 and recovering the protein from said cells.

* * * * *